(12) United States Patent
Fencel

(10) Patent No.: US 8,343,083 B1
(45) Date of Patent: Jan. 1, 2013

(54) AUTO-FLEX KNEE BRACE

(76) Inventor: Stanley R Fencel, Irvine, CA (US)

( * ) Notice: Subject to any disclaimer, the term of this patent is extended or adjusted under 35 U.S.C. 154(b) by 274 days.

(21) Appl. No.: 12/950,949

(22) Filed: Nov. 19, 2010

(51) Int. Cl.
*A61F 5/00* (2006.01)
(52) U.S. Cl. ............................. 602/23; 602/26
(58) Field of Classification Search ............... 602/5, 16, 602/23, 26; 128/882; 482/122
See application file for complete search history.

(56) References Cited

U.S. PATENT DOCUMENTS

| | | | | |
|---|---|---|---|---|
| 2,591,373 A | * | 4/1952 | Petruch | 602/26 |
| 3,026,869 A | * | 3/1962 | Peach | 602/16 |
| 4,624,246 A | * | 11/1986 | Ajemian | 602/26 |
| 4,773,404 A | | 9/1988 | Townsend | |
| 5,013,037 A | * | 5/1991 | Stermer | 482/122 |
| 6,471,664 B1 | * | 10/2002 | Campbell et al. | 602/16 |
| 6,875,187 B2 | | 4/2005 | Castillo | |
| 7,662,122 B2 | | 2/2010 | Sterling | |

\* cited by examiner

*Primary Examiner* — Michael A. Brown
(74) *Attorney, Agent, or Firm* — W. D. English

(57) ABSTRACT

An auto-flex knee brace that employs an extension spring defined as a flexible hinge, which determines different modes of configuration to alleviate medial and lateral compartmental osteoarthritis of a knee of a patient is disclosed. The auto-flex knee brace comprises an upper thigh cuff, a lower thigh cuff, a flexible strap arrangement and at least one spring column assembly. The upper thigh cuff is positioned substantially above knee for encircling an upper part of leg of a user and the lower thigh cuff is positioned substantially below the knee for encircling a lower part of the leg of the user. The flexible strap arrangement includes a first strap means and a second strap means that securely tied around the upper thigh cuff and the lower thigh cuff. The at least one spring column assembly is adaptable for releasably coupling the upper thigh cuff and the lower thigh cuff.

27 Claims, 74 Drawing Sheets

AUTO-FLEX KNEE BRACE

CROSS-REFERENCE TO RELATED APPLICATIONS

Not Applicable.

STATEMENT REGARDING FEDERALLY SPONSORED RESEARCH AND DEVELOPMENT

Not Applicable.

FIELD OF THE INVENTION

This invention relates to knee braces, and more particularly to an auto-flex knee brace that employs an extension spring defined as a flexible hinge, which determines different modes of configuration to alleviate medial and lateral compartmental osteoarthritis of a knee of a patient.

DISCUSSION OF RELATED ART

The knee is the body's primary weight-bearing joint and is one of the most frequently injured joints. The medial-collateral and anterior-cruciate ligaments are the major stabilizers of the knee and can be injured when forces are applied to the knee. Several types of knee braces are available that may be utilized in treating patients with injuries or disorders of the knee. The brace can be constructed from a variety of materials, such as foam, metal, plastic, elastic material or straps. The knee brace includes three basic components such as a cuff member, a hinge, and a strap system. A knee brace is defined as an orthosis or orthopedic appliance that supports or holds in correct position any movable part of the body and that allows for motion of that part. Generally, the knee braces may be classified according to the function they perform. Prophylactic braces are designed to prevent or reduce the severity of knee injury. The objective of using a prophylactic knee brace is to prevent or reduce the severity of injury to a healthy knee. The prophylactic knee brace is generally indicated for protection of the medial-collateral ligament (MCL) against valgus knee stresses and ACL protection from rotational stress in similar situations. Functional braces are designed to provide stability for the anterior-cruciate ligament (ACL) or other ligament deficiency of the knee. Rehabilitative braces are designed to allow protected motion of injured knees or knees that have been treated operatively and the unloader/offloader braces are designed to provide pain relief in arthritic knees.

Knee braces are provided in a variety of design variations and are known in the art. U.S. Pat. No. 4,773,404 issued to Townsend on Sep. 27, 1988 provides an appliance for controlling an unstable knee joint in the sagittal, coronal and transverse planes, comprising femoral and tibial cuffs joined by links that are interconnected to provide a novel mechanical joint. The camming slots are formed in one of the links with cams disposed on the other link, the slots comprising straight segments and arcuate segments so as to provide approximately 8 millimeters of sliding movement between the femur and tibia, followed by relative rotation about the center of radius of the femoral condyle as the leg is flexed. The tibial cuff is conformed about the boney prominence or shin of the tibia to inhibit rotation of the leg beneath the knee within the brace itself. The hinge mechanism of the knee brace controls movement within a single plane, but fails to control other planes of motion of the knee joint.

U.S. Pat. No. 6,875,187 issued to Castillo on Apr. 5, 2005 discloses a knee brace including a lateral hinge component and a medial hinge component, a lower member encompassable about a lower leg portion and having a lateral element and a medical element each extending upwardly and connectingly engaged respectively to the hinge components, an upper member encompassable about an upper leg portion and having a lateral element extending downwardly and connectingly engaged to the lateral hinge component and a medial element extending downwardly to a distal end terminating above the medial hinge component. A medially disposed arm is connectingly engaged to the medial hinge component and extends upwardly from the hinge component to be adjacent the medial element of the upper member for connection to each other with a releasably securable slidable engager. The arm and medial element are slidable and securable against each other to thereby laterally inwardly, outwardly position the upper member in angular relationship to the lower member, and consequently treat inward or outward leg curvature through correction of knee joint orientation. However, the knee brace lacks the rigidity necessary to properly brace the knee joint. The hinges of the knee brace are not rigidly fixed relative to one another. The medial and lateral hinges are provided independently in medial and lateral cuffs and are held together by flexible straps. This knee brace therefore does not provide the freedom of movement of knee joint.

U.S. Pat. No. 7,662,122 issued to Sterling on Feb. 16, 2010 disclose an orthotic knee brace for treating unicompartmental osteoarthritis in a knee joint is described. The brace includes a fabric sleeve mounting and a bracing member removably positioned in the sleeve to provide a therapeutic force on the joint. The force is applied by a force dosimeter assembly that draws an incrementally adjustable amount of force on cables connected to the bracing member. The brace includes a ratchet assembly comprises a pawl and a plurality of splines and tensioning component including a plurality of spring gears. However, it is difficult to support a wide range of knee motion because the gears and pawls must be correctly installed and maintained. Since the hinges are precision aligned with complex gear/pawl mechanism, it is very difficult the bowed or knock knees, i.e. valgus and varus deformities. This invention is not applicable for obese patients because of surplus flesh that prevents accuracy of various functions and the brace cannot accurately follow the knee adduction moments. The adjustment of the knee brace is tending to be somewhat cumbersome and time consuming.

Some of the conventional knee braces includes the thigh and calf support members formed from two adjustably interconnectable longitudinal sections that may be intersecured in selectively variable positions to thereby alter the length of each of the four support members. However, the interconnection between the two longitudinal sections of each of the support members cause inconvenience and laborious while adjusting the brace and has been prone to slippage. Various removable locking members have been utilized to provide a secure interconnection between the two longitudinal sections, but such locking members have the tendency to loosen and result in dislodgement during use of the brace. When the interconnection in the brace subsequently fails to properly restrain its pivotal motion then it will cause damage to the knee.

Therefore, there is a need for an auto-flex knee brace that employs an extension spring defined as a flexible hinge, which determines different modes of configuration to alleviate medial and lateral compartmental osteoarthritis of a knee of a patient. Such a knee brace would use for offloader, prophylactic, rehabilitative and functional brace applications. Such a device would reduce excessive knee cuff movements, possible subsequent damage to ACL (anterior cruciate ligament), MCL (medial collateral ligament), and other ligaments. Such brace would support a wide range of knee motion and provide easy adjustment of the length of the flexible hinge. Moreover, the knee brace would not slip out of position or bind because of a flexible strap arrangement and a spring column assembly. The present invention accomplishes these objectives.

SUMMARY OF THE INVENTION

The present invention is an auto-flex knee brace that employs an extension spring defined as a flexible hinge, which determines different modes of configuration to alleviate medial and lateral compartmental osteoarthritis of a knee of a patient. The auto-flex knee brace comprises an upper thigh cuff, a lower thigh cuff, a flexible strap arrangement and at least one spring column assembly. The upper thigh cuff is positioned substantially above knee for encircling an upper part of leg of a user and the lower thigh cuff is positioned substantially below the knee for encircling a lower part of the leg of the user. The flexible strap arrangement includes a first strap means attached to a hinged retainer on the upper thigh cuff and a second strap means attached to a hinged retainer on the lower thigh cuff. The first strap means and the second strap means is tied around the upper thigh cuff and the lower thigh cuff using a Velcro means. The at least one spring column assembly is adaptable for releasably coupling the upper thigh cuff and the lower thigh cuff.

Each of the spring column assembly comprises an extension spring, a lower cuff connection rod, an extension connection rod, an adjustable knob and an upper cuff connection rod. The upper thigh cuff and the lower thigh cuff include an extended inner liner material on borders thereof to reduce the pressure generated by the flexible strap arrangement. The extension spring having a proximal end and a distal end acts as a flexible hinge. The lower cuff connection rod has a pair of terminal ends, one end being threaded and the other end features a half flat portion. The cylindrical threaded end is tightly screwed into the proximal end of the extension spring. The extension connection rod has a first end, a second end and a longitudinally arranged threaded screw hole. The first end is tightly screwed into the distal end of the extension spring.

The adjustable knob includes a threaded compartment and a non threaded compartment separated by a screw hole partition. The non threaded compartment is connected to the second end of the extension connection rod through the threaded screw hole utilizing at least one fastening means. The at least one fastening means may be a screw. The upper cuff connection rod has a pair of terminal ends, one end being threaded and the other end featuring a half flat portion. The cylindrical threaded end is tightly screwed into the threaded compartment of the adjustable knob. The at least one spring column assembly is configured to mount at different relative vertical positions and modes between the upper and lower thigh cuffs thereby achieving a surgery-free way of promoting autogenously as well as supplement-induced knee cartilage cell production in a non-bone-scraping environment.

The half flat portion of the lower cuff connection rod includes at least one screw aperture. The lower connection rod is attached with the lower thigh cuff through the screw aperture using at least one attachment means. The at least one attachment means may be a screw. The lower thigh cuff includes a slot having a top notch and a bottom notch. The lower cuff connection rod slides through the slot and connects to the top notch or the bottom notch through the at least one screw aperture utilizing at least one attachment means. The upper thigh cuff includes a slot having a plurality of screw apertures. The upper cuff connection rod slides through the slot and connects to the plurality of notches through the plurality of screw apertures utilizing the at least one attachment means. The cylindrical threaded end of the upper cuff connection rod has a narrow channel region below thread depth lengthwise to accommodate a graduation scale that indicates distance traveled when the adjustable knob is rotated.

The at least one mode of configuration may be a push-push mode, a pull-pull mode and push-pull mode. In push-push mode, each of the spring column assembly is attached to the top notch using the at least one attachment means and the length of the spring column assembly is reduced using the adjustable knob that pushes both sides of the upper cuffs and both sides of the lower cuffs apart. In pull-pull mode, each of the spring assembly is attached to the bottom notch using the at least one attachment means and the length of the spring column assembly is reduced using the adjustable knob that pulls both sides of the upper cuffs and both sides of the lower cuffs together. In push-pull mode, one of the spring column assembly is attached to the top notch and another spring column assembly is attached to the bottom notch using the at least one attachment means and the length of the spring column assembly attached to the top notch is increased to achieve a push on one side of the cuffs and the length of the spring column assembly attached to the top notch is reduced to achieve pull on other side of the cuffs using the adjustable knob.

The human knee is constructed so that ligaments, tendons, and muscles attach the upper articulating femoral section to the lower tibia knee section and serve as a "floating" anchor support system without a fixed, pressed-in-place anchor. Therefore, the angle of the femur bone can be altered by adjusting the spring column assembly's lengths to generate different size forces on each side of the cuffs. The higher thigh angle results in an increased condylar gap on that side of the knee. This allows for customization of the auto-flex knee brace to any bone wear pattern.

DESCRIPTION OF THE DRAWINGS

FIG. 4a is an exploded view of the at least one spring column assembly shown in FIG. 3a;

FIG. 5 is an enlarged view of a lower cuff connection rod with at least one screw aperture shown in FIG. 3a;

FIG. 6 is an enlarged view of an extension spring shown in FIG. 3a;

FIG. 10 is an enlarged view of an adjustable knob shown in FIG. 3a;

FIG. 16 is an enlarged view of the upper cuff connection rod with a plurality of screw apertures shown in FIG. 3a;

FIG. 32b illustrates a left side view and a right side view of the embodiment shown in the FIG. 32a;

FIG. 35b illustrates a left side view and a right side view of the embodiment shown in the FIG. 35a;

FIG. 37b illustrates a left side view and a right side view of the embodiment shown in the FIG. 37a;

DETAILED DESCRIPTION OF THE PREFERRED EMBODIMENT

Figure 1:
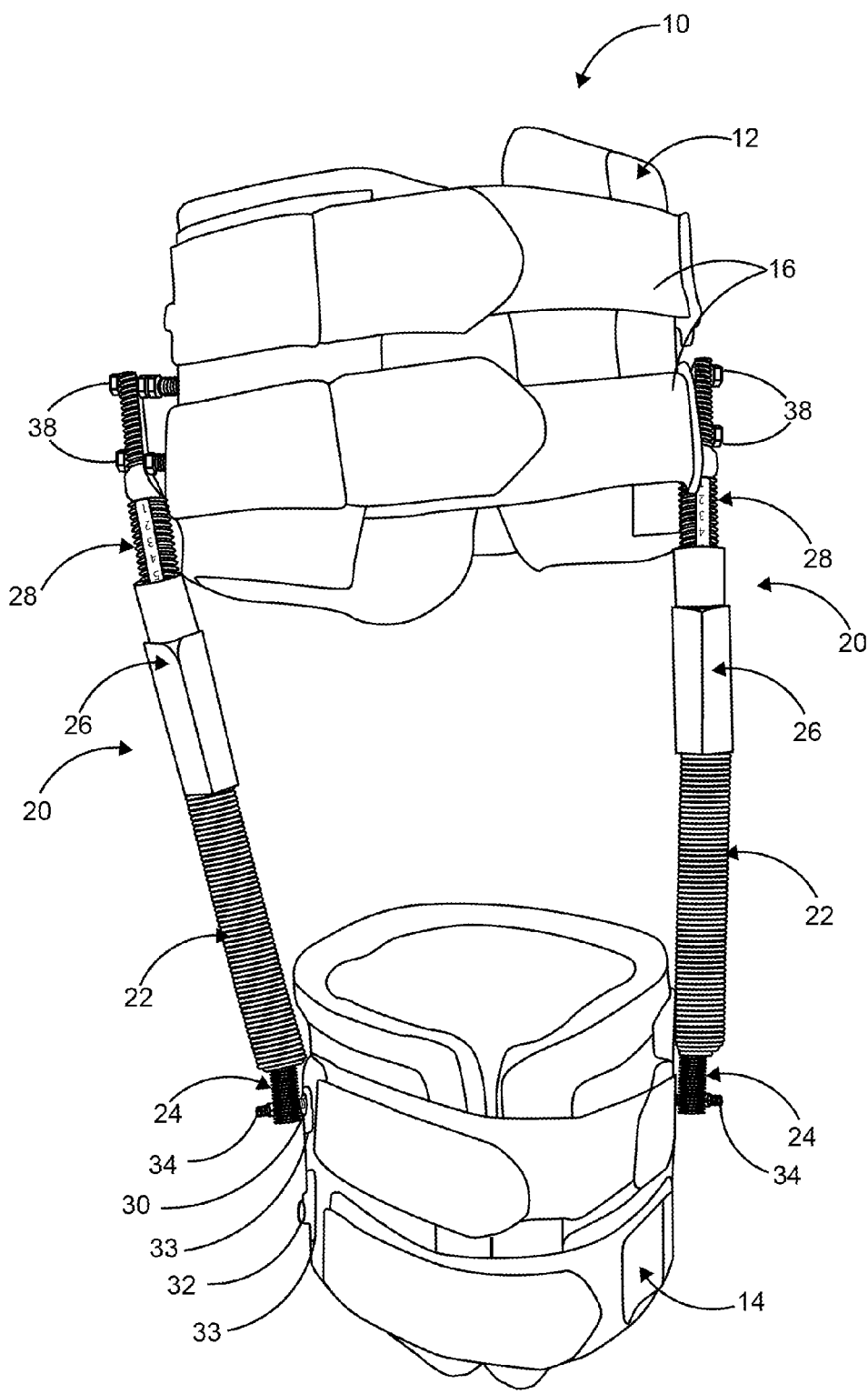
FIG. 1 is a front perspective view of the present invention, illustrating an upper thigh cuff and a lower thigh cuff with straps tied.
Figure 2A:
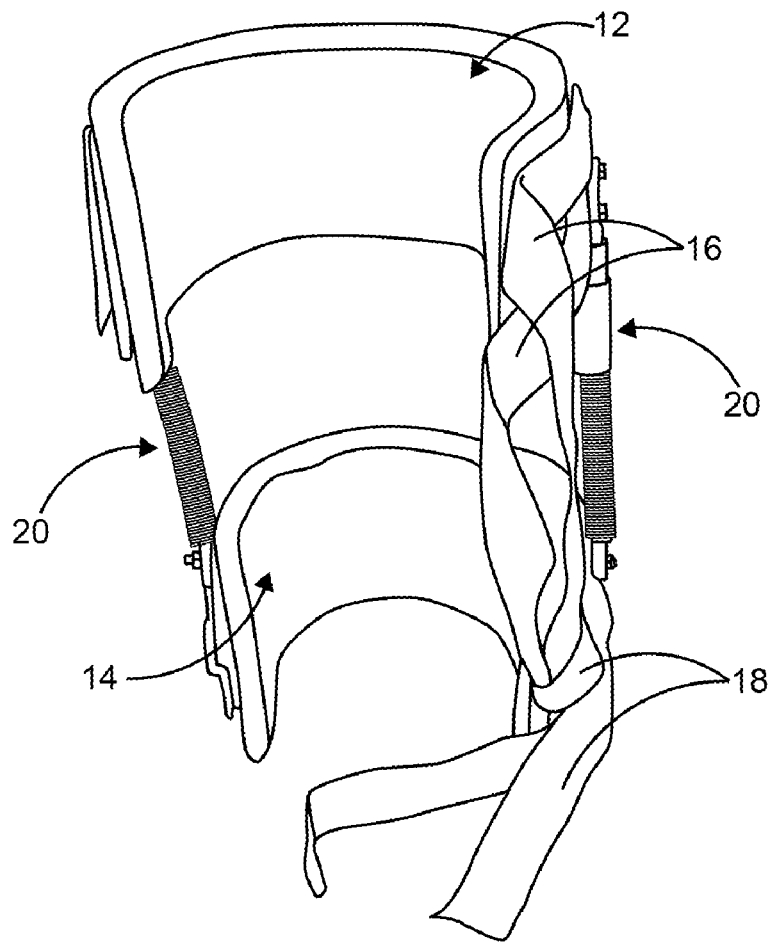
FIG. 2a is a front perspective view of the present invention, illustrating the upper thigh cuff and the lower thigh cuff with the straps untied.
Figure 2B:
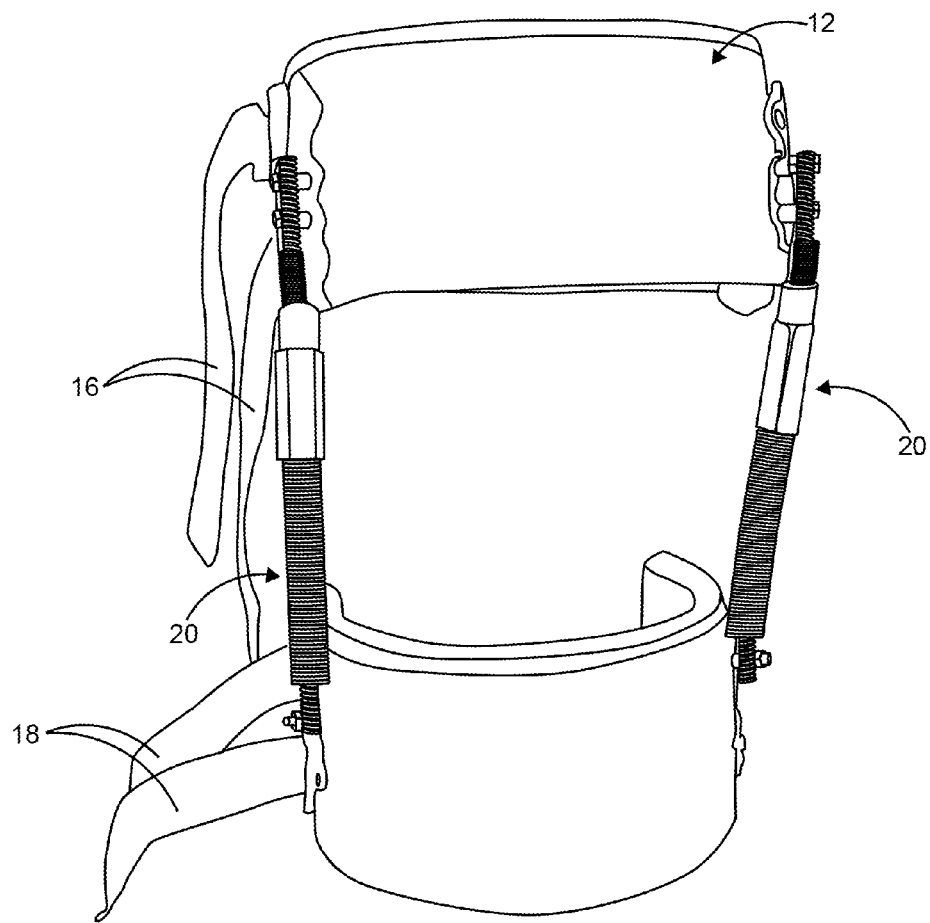
FIG. 2b is a rear perspective view of the present invention, illustrating the upper thigh cuff and the lower thigh cuff with the straps untied.

Referring to the drawings, a preferred embodiment illustrates an auto-flex knee brace 10 that employs an extension spring defined as a flexible hinge, which determines different modes of configuration to alleviate medial and lateral compartmental osteoarthritis of a knee of a patient, and generally indicated in FIGS. 1 through 31. The different embodiments of the present invention are illustrated and indicated in FIGS. 32a through 37d. The auto-flex knee brace 10, shown by way of examples of the modes of configuration achieved by adjusting the components, is adapted for placement of the leg to reduce the excessive knee movements and possible subsequent damage to anterior cruciate ligament, medial collateral ligament and other ligaments. Referring to FIGS. 1, 2a and 2b, the auto-flex knee brace 10 comprises an upper thigh cuff 12, a lower thigh cuff 14, a flexible strap arrangement 16, 18 and at least one spring column assembly 20.

The upper thigh cuff 12 is positioned substantially above the knee for encircling an upper part of leg of a user and the lower thigh cuff 14 is positioned substantially below the knee for encircling a lower part of the leg of the user. The upper thigh cuff 12 includes a slot (not shown) having a plurality of notches (not shown). The lower thigh cuff 14 includes a slot 33 having a top notch 30 and a bottom notch 32. The flexible strap arrangement 16, 18 includes a first strap means 16 attached to a hinged retainer on the upper thigh cuff 12 and a second strap means 18 attached to a hinged retainer on the lower thigh cuff 14. The at least one spring column assembly 20 is adaptable for releasably coupling the upper thigh cuff 12 and the lower thigh cuff 14. Each of the spring column assembly 20 comprises an extension spring 22, a lower cuff connection rod 24, an extension connection rod (not shown), an adjustable knob 26 and an upper cuff connection rod 28.

The upper and lower thigh cuffs 12, 14 include an extended inner liner material on borders thereof to reduce the pressure generated by the flexible strap arrangement 16, 18. The extended inner liner material may be formed from natural gum foam strips. The extended inner liner material has a high friction silicone rubber contact sheet bonded to the natural gum foam strips providing an additional gripping power to prevent the auto-flex knee brace 10 migrations. The use of the silicone rubber contact sheet is not the only friction-enhancing liner that could be used. Friction in the upper and lower thigh cuffs 12, 14 can be further increased by applying water-resistant, non-irritating lotion to the extended inner liner. Friction can also be enhanced by removing body oils and perspiration from the user's leg. This can be accomplished by applying rubbing alcohol to the skin.

The extended inner liner material decrease the pound force per assigned area, thereby promoting circulation, reducing intramuscular pressure generated by leg and the first strap means 16 and second strap means 18 on soft tissue and retard rotational migration with increased gripping area. The extended inner liners of both the upper and lower thigh cuffs 12, 14 are formed from natural gum foam strips with open cell structures in which each cell connects to another cell providing a path for water, air, perspiration etc. to circulate through the outside surface for added cooling.

Figure 3A:
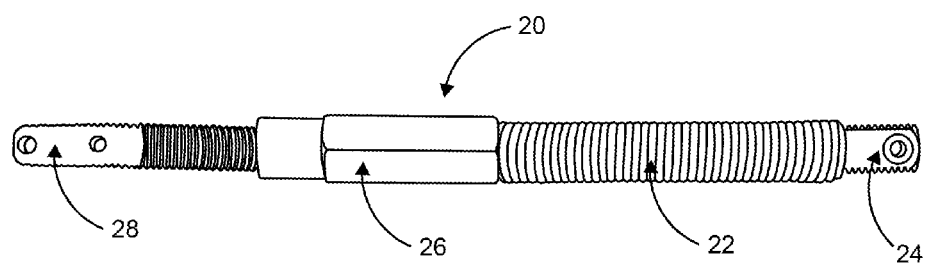
FIG. 3a is a side perspective view of at least one spring column assembly of the present invention.
Figure 3B:
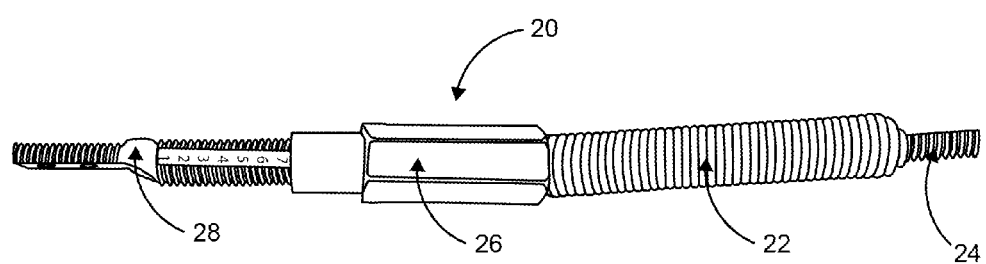
FIG. 3b is a side perspective view showing the at least one spring column assembly with a graduation scale.

FIGS. 3a and 3b illustrate the at least one spring column assembly 20 which is in a completely assembled state. One end of the spring column assembly 20 is attached to the upper thigh cuff 12 and other end is attached to the lower thigh cuff 14. The at least one spring column assembly 20 is created from incompressible steel thereby providing maximum weight support and flexibility.

In the relaxed state, the spring column assembly 20 is a compressed flexible solid beam. Each of the spring column assembly 20 is mounted on fixed positions on both the thigh cuffs 12, 14. The spring column assembly 20 changes their bending central axis location automatically and accommodates the entire knee flexion range.

Figure 4A:
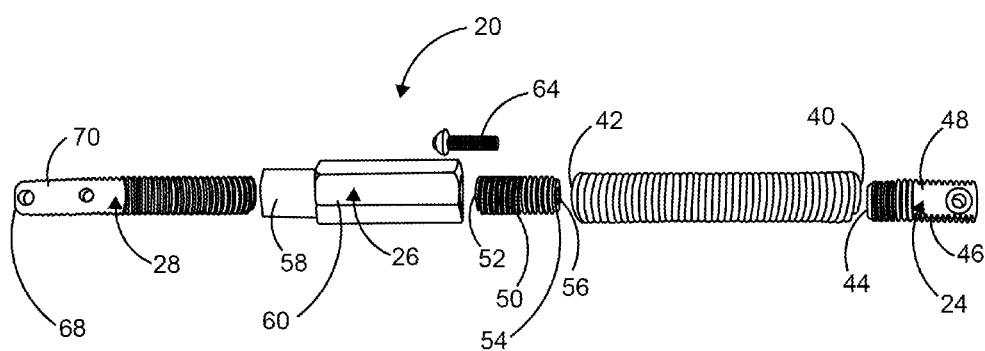
Figure 4B:
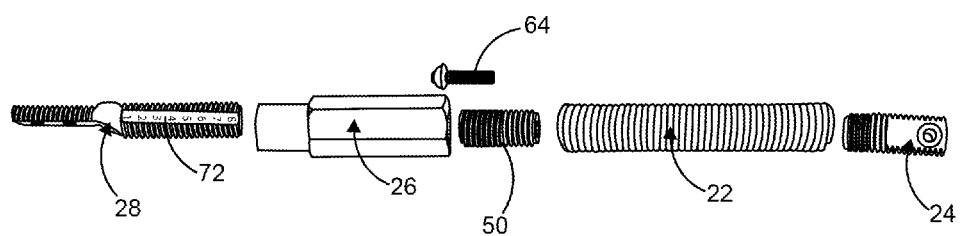
FIG. 4b is an exploded view of the at least one spring column assembly shown in FIG. 3b.

FIGS. 4a and 4b illustrate the at least one spring column assembly 20 which is completely disassembled. The spring column assembly 20 comprises the extension spring 22, the lower cuff connection rod 24, the extension connection rod 50, the adjustable knob 26 and the upper cuff connection rod 28. Each of the components is arranged in a fixed compression mode with no gaps and acts as a compressed solid column that is flexible and connects together the upper thigh cuff 12 and the lower thigh cuff 14. The extension spring 22 having a proximal end 40 and a distal end 42 acts as a flexible hinge. The lower cuff connection rod 24 has a pair of terminal ends 44, 46, one end being threaded and the other end featuring a half flat portion 48. The cylindrical threaded end 44 is tightly screwed into the proximal end of the extension spring 40.

The extension connection rod 50 has a first end 52, a second end 54 and a longitudinally arranged threaded screw hole 56. The first end 52 is tightly screwed into the distal end of the extension spring 42. The adjustable knob 26 includes a threaded compartment 58 and a non threaded compartment 60 separated by a screw hole partition 62. The non threaded compartment 60 is connected to the second end of the extension connection rod 54 through the threaded screw hole 56 utilizing at least one fastening means 64. The at least one fastening means 64 may be a screw. The upper cuff connection rod 28 has a pair of terminal ends 66, 68, one end being threaded and the other end featuring a half flat portion 70. The cylindrical threaded end of the upper cuff connection rod 66 has a narrow channel region below thread depth lengthwise to accommodate a graduation scale 72 that indicates the distance traveled when the adjustable knob 26 is rotated. The cylindrical threaded end 66 is tightly screwed into the threaded compartment of the adjustable knob 58. The at least one spring column assembly 20 is configured to mount at different relative vertical positions and modes between the upper and lower thigh cuffs 12, 14 thereby achieving a surgery-free way of promoting autogenously as well as supplement-induced knee cartilage cell production in a non-bone-scraping environment.

Figure 5:
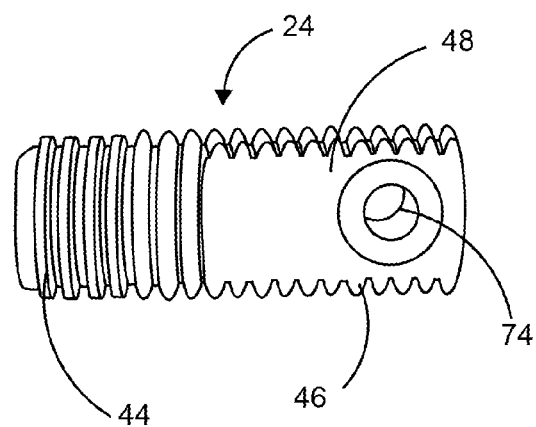

FIG. 5 is an enlarged view of the lower cuff connection rod 24. The half flat portion of the lower cuff connection rod 48 includes at least one screw aperture 74. The lower cuff connection rod 24 is attached with the lower thigh cuff 14 through the screw aperture 74 using at least one attachment means 34. The at least one attachment means 34 may be a screw. The size of threads of the lower cuff connection rod 24 matches the internal diameter of the extension spring 22. The lower thigh cuff 14 includes the slot 33 having the top notch 30 and the bottom notch 32. The lower cuff connection rod 24 slides through the slot 33 and connects to the top notch 30 or the bottom notch 32 through the at least one screw aperture 74 utilizing the at least one attachment means 34.

Figure 6:
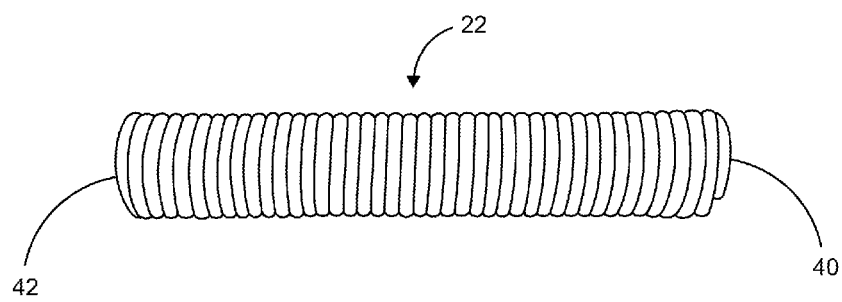

FIG. 6 is an enlarged view of the extension spring 22. The extension spring 22 acts as a flexion hinge thereby automatically assume a center position of least resistance and not hinder knee flexing motion. Low resistance flexion allows the steel spring column assembly 20 to be bent smoothly and easily. The extension spring 22 acts as a multi-axial hinge that automatically merges into the correct channel configuration without friction or additional power requirements.

Figure 7:
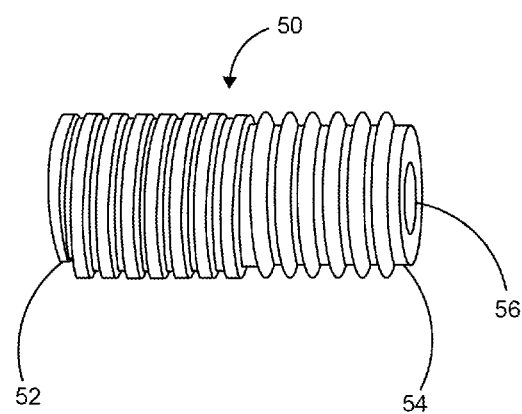
FIG. 7 is an enlarged view of an extension connection rod shown in FIG. 3a in which a second end of the extension connection rod does not needed to be threaded.
Figure 8:
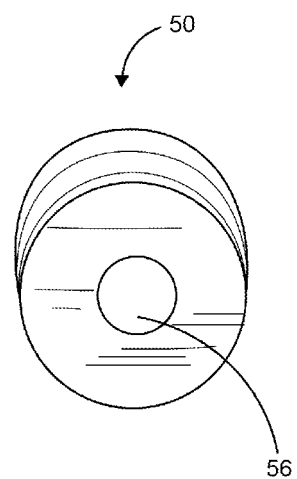
FIG. 8 is an enlarged view of a longitudinally arranged threaded screw hole of the extension connection rod shown in FIG. 7.

FIGS. 7 and 8 illustrate enlarged views of an extension connection rod 50. The extension connection rod 50 is cylindrical in shape and includes a longitudinally arranged screw hole 56. The second end of the extension connection rod 54 is screwed on the at least one fastening means 64 exiting from the non threaded compartment of the adjustable knob 60. The second end of the extension connection rod 54 does not have to be threaded.

Figure 9:
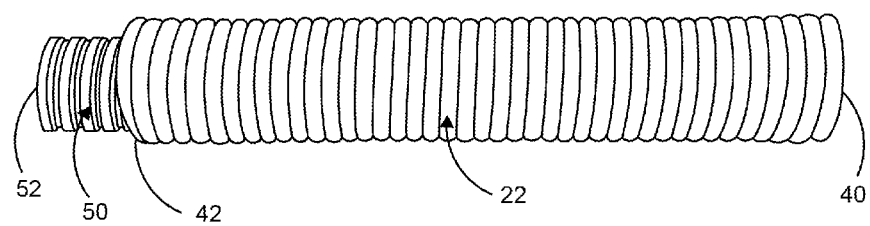
FIG. 9 illustrates diagrammatically in a perspective view the extension connection rod and the extension spring screwed together in accordance with the present invention.

Referring to FIG. 9, the cylindrical threaded first end of the extension connection rod 52 is screwed into the extension spring 22 that acts as an interconnecting rod that provides length for the spring column assembly 20 to couple both the thigh cuffs 12, 14.

Figure 10:
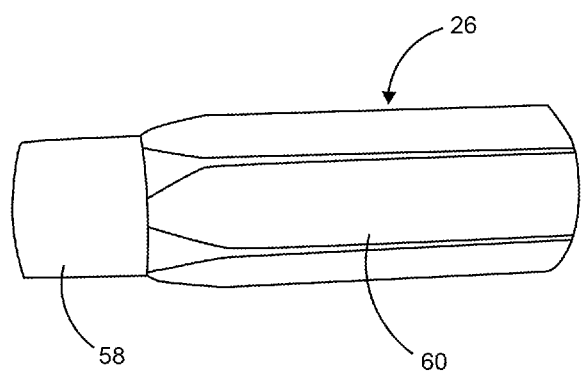

FIG. 10 is an enlarged view of the adjustable knob 26. The adjustable knob 26 is made from hexagon stock to provide either a hand/wrench adjusting wrench. The hexagon adjustable knob 26 can be turned for adjusting the length of the spring column assembly 20 and when the knee flexes, the extension spring 22 will bend as necessary to accommodate the newly formed arc as required. The adjustment of the length of the spring column assembly 20 determines at least one mode of configuration of the auto-flex knee brace 10.

Figure 11:
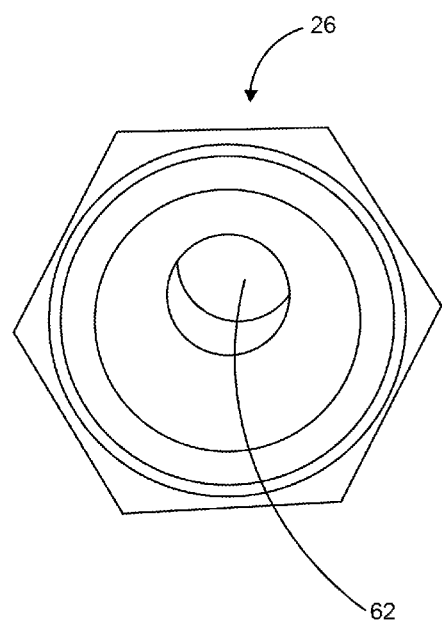
FIG. 11 is an enlarged view of a non-threaded compartment of the adjustable knob shown in FIG. 10.
Figure 12:
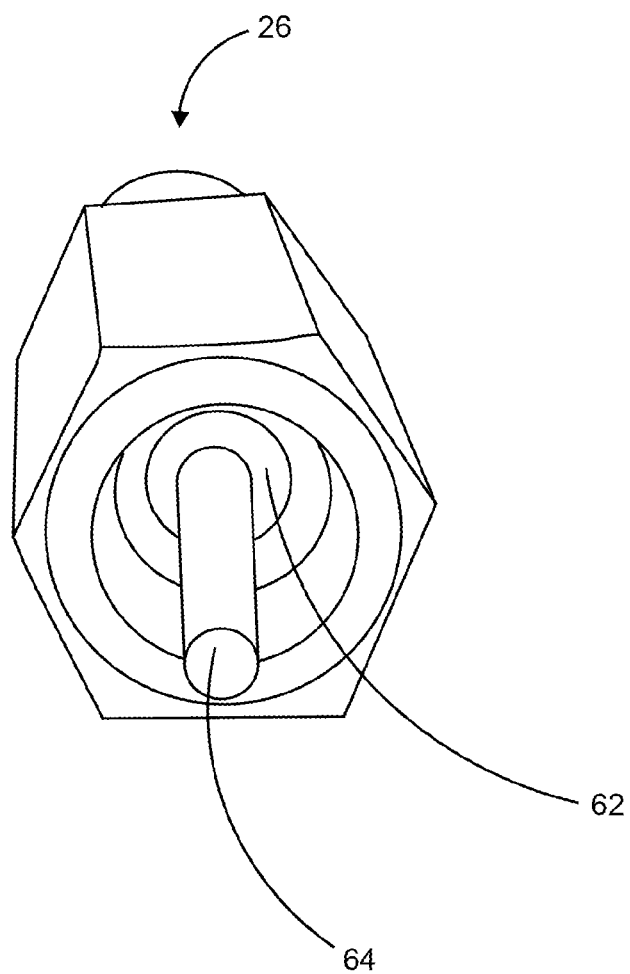
FIG. 12 is an enlarged view showing at least one fastening means exiting from the non-threaded compartment of the adjustable knob shown in FIG. 10.
Figure 13:
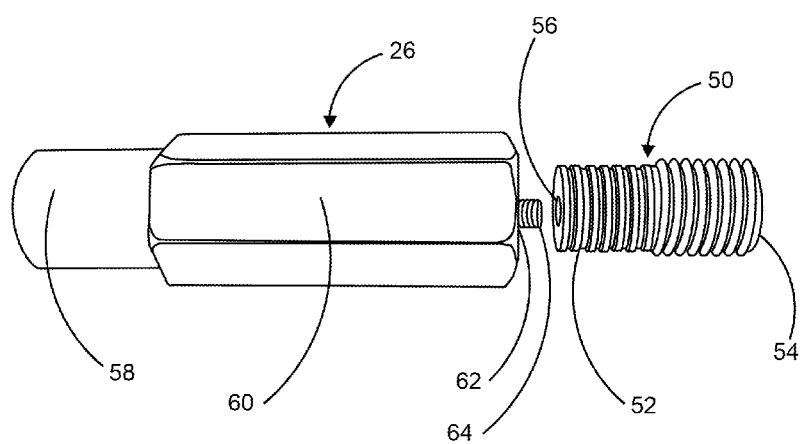
FIG. 13 illustrates diagrammatically in a perspective view at least one fastening means exiting in the non-threaded compartment of the adjustable knob and the extension spring intended to be screwed together in accordance with the present invention.

FIGS. 11, 12 and 13 illustrate enlarged views of a non-threaded compartment of the adjustable knob 60. At least one fastening means 64 exiting from the screw hole partition 62 of the non-threaded compartment of the adjustable knob 60 is screwed into the second end of the extension connection rod 54.

Figure 14:
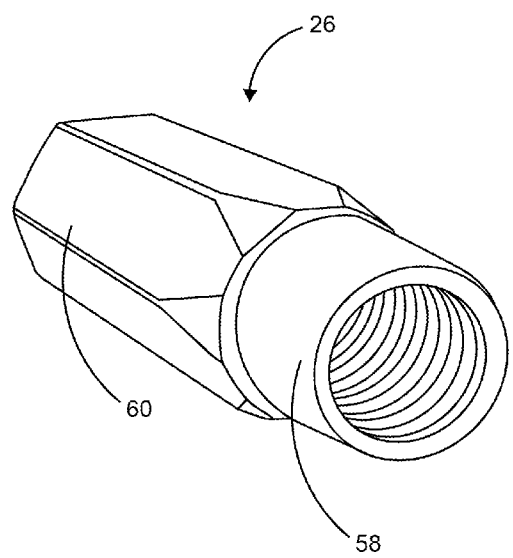
FIG. 14 is an enlarged view of a threaded compartment of the adjustable knob shown in FIG. 10.
Figure 15A:
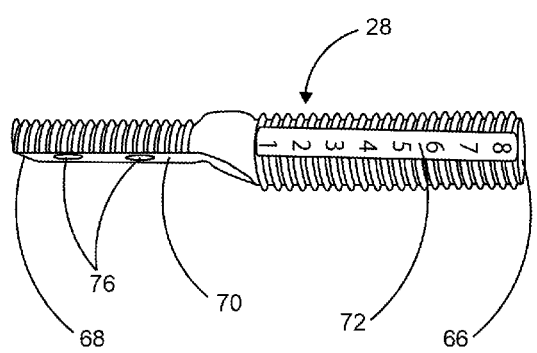
FIG. 15a is an enlarged view of an upper cuff connection rod with the graduation scale shown in FIG. 3b.
Figure 15B:
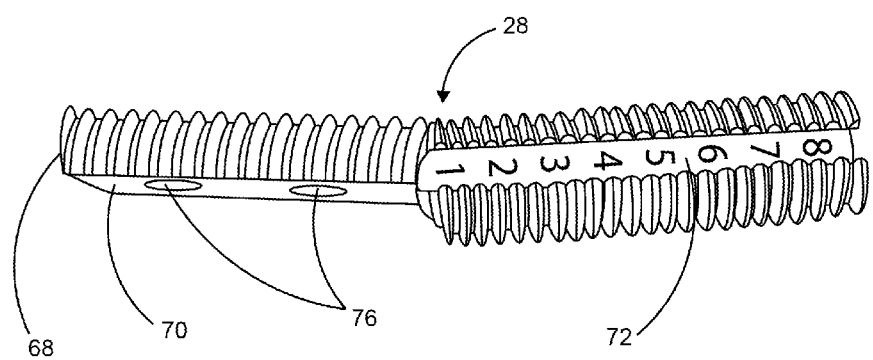
FIG. 15b is an enlarged view of the upper cuff connection rod in which the graduation scale is slightly angled.
Figure 16:
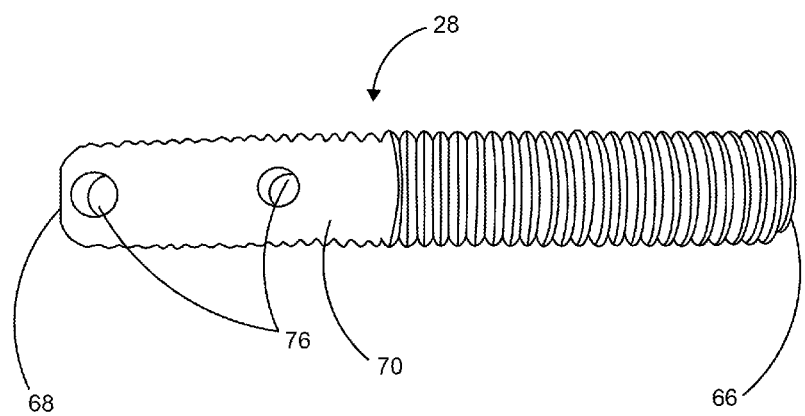
Figure 17:
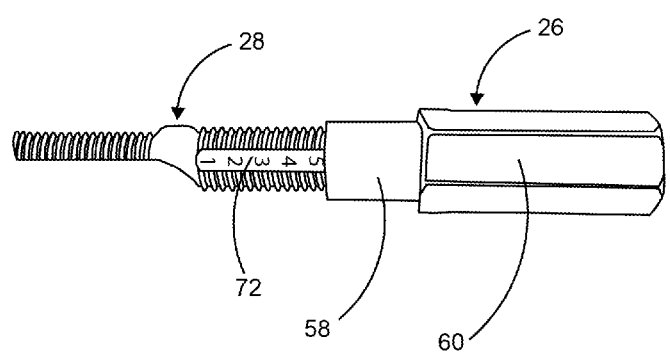
FIG. 17 illustrates diagrammatically in a perspective view the upper cuff connection rod and threaded compartment of the adjustable knob screwed together in accordance with the present invention.

FIG. 14 is an enlarged view of a threaded compartment of the adjustable knob 58. The threaded compartment 58 receives the cylindrical threaded end of the upper cuff connection rod 66. The depth of the screw hole of the extension connection rod 56 received the fastening means 64 exiting from the non-threaded end of the adjustable knob 60 are calculated so that the threaded end of the adjustable knob 58 can freely rotate in without excessive play.

FIGS. 15a, 15b, 16 and 17 illustrate enlarged views of an upper cuff connection rod 28. The half flat portion of the upper cuff connection rod 70 includes a plurality of screw apertures 76 thereof. The upper thigh cuff 12 includes the slot (not shown) having the plurality of notches (not shown). The upper cuff connection rod 28 slides through the slot (not shown) and connects to the plurality of notches (not shown) through the plurality of screw apertures 76 utilizing the at least one attachment means 38. The cylindrical threaded end of the upper cuff connection rod 66 has a narrow channel region below thread depth lengthwise to accommodate the graduation scale 72 that indicates distance traveled when the adjustable knob 26 is rotated. The upper cuff connection rod 28 that is slightly angled can be used in the right-hand spring column assembly 20 for patient with valgus deformities (bow-legged). Normal patients may use a straight right-hand upper cuff connection rod 28.

Figure 18:
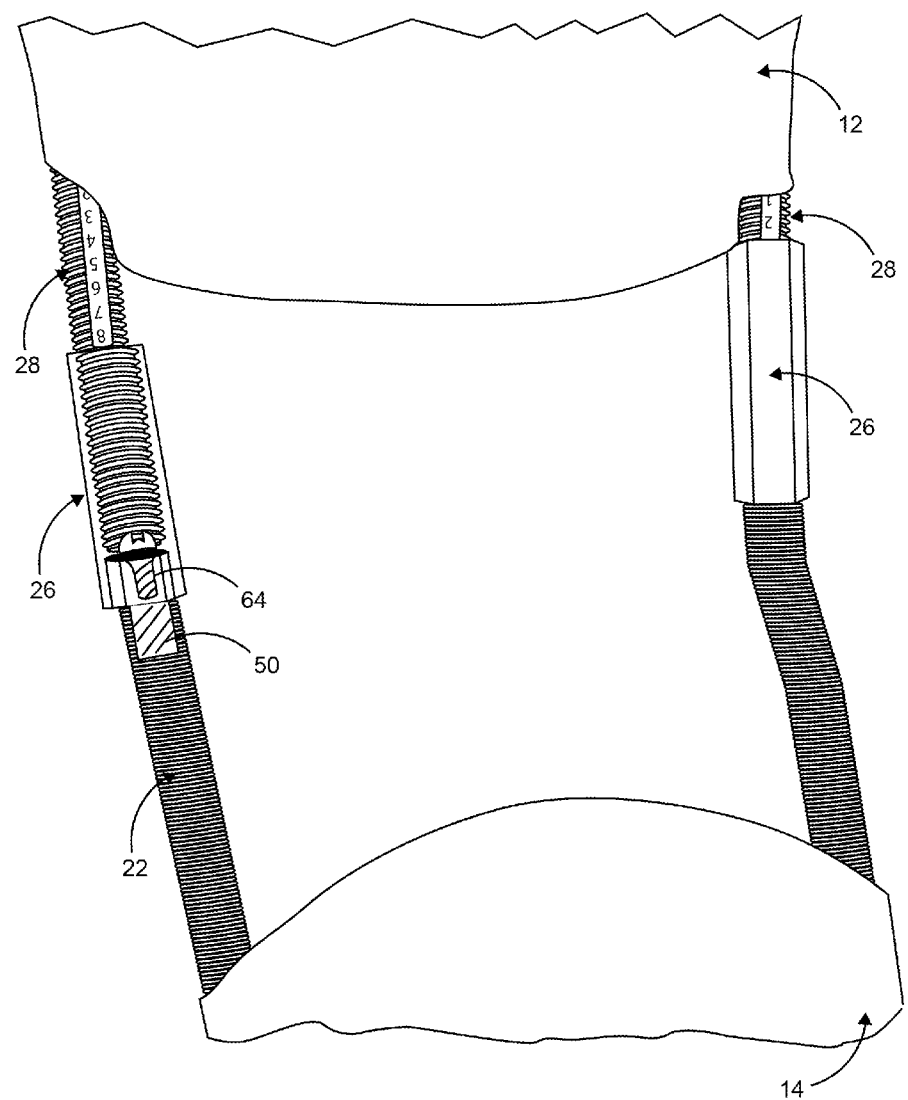
FIG. 18 is a cut away view showing the internals of the at least one spring column assembly in its assembled state.
Figure 19A:
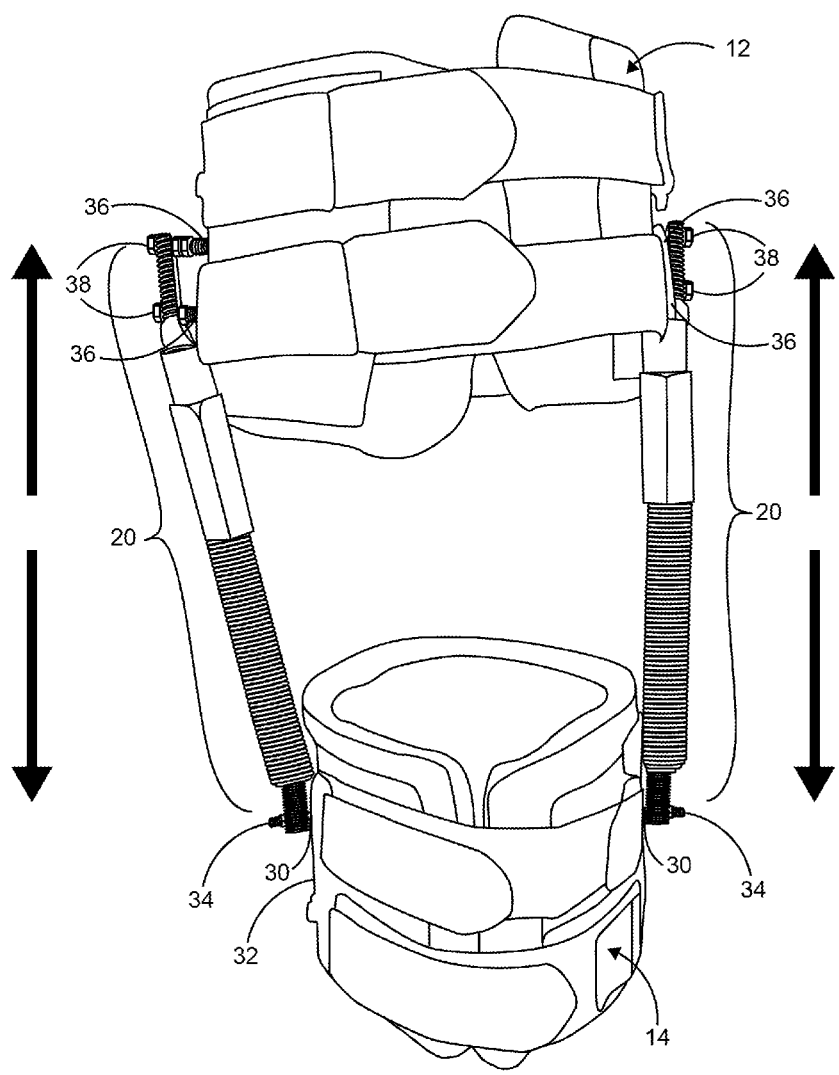
FIG. 19a illustrates a push-push mode of configuration of the present invention applied in an offloader exerting a minimal force.
Figure 19B:
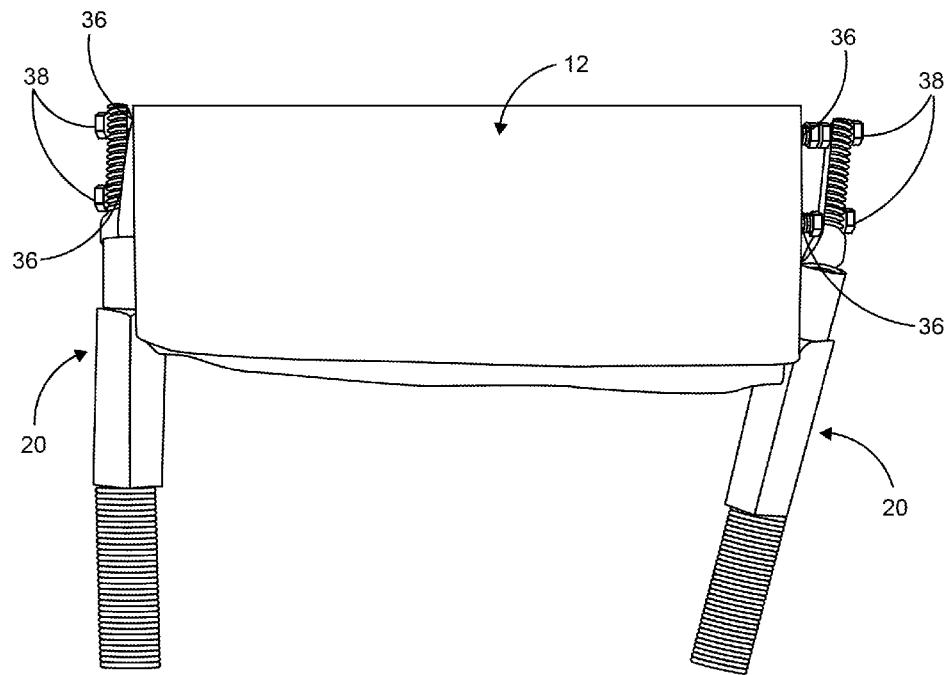
FIG. 19b illustrates a close-up view of the push-push mode of configuration of the present invention applied in the offloader exerting the minimal force.
Figure 19C:
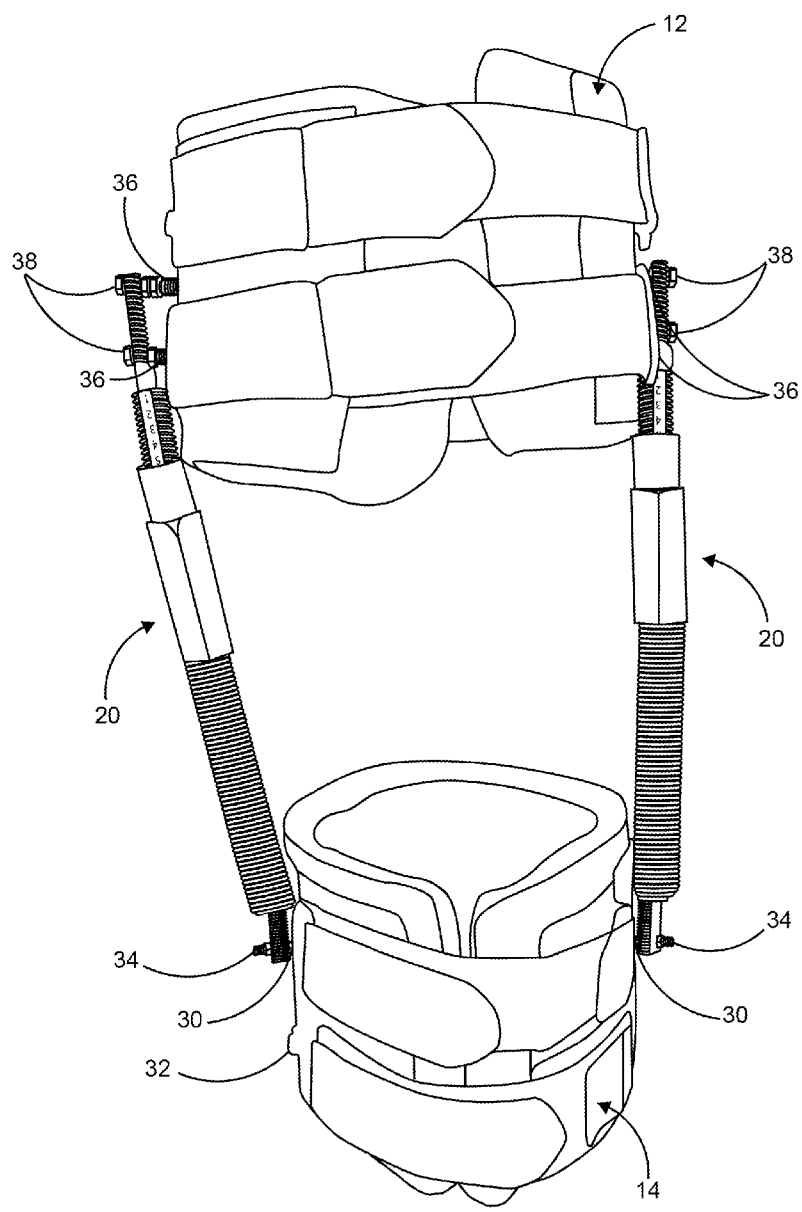
FIG. 19c illustrates the push-push mode of configuration of the present invention applied in the offloader exerting a medium force.
Figure 19D:
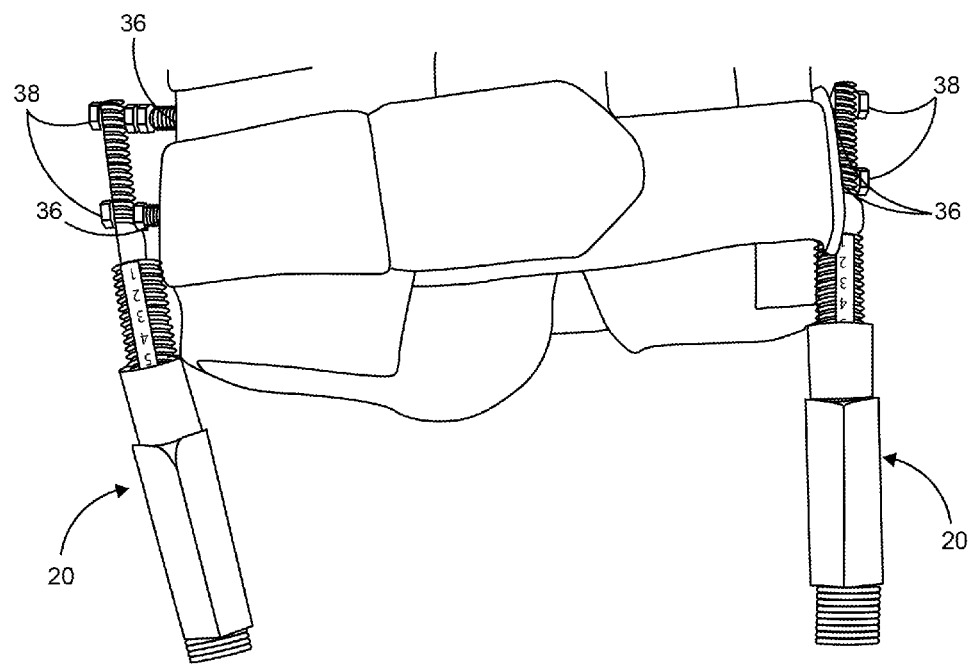
FIG. 19d illustrates a close-up view of the push-push mode of configuration of the present invention applied in the offloader exerting the medium force.
Figure 19E:
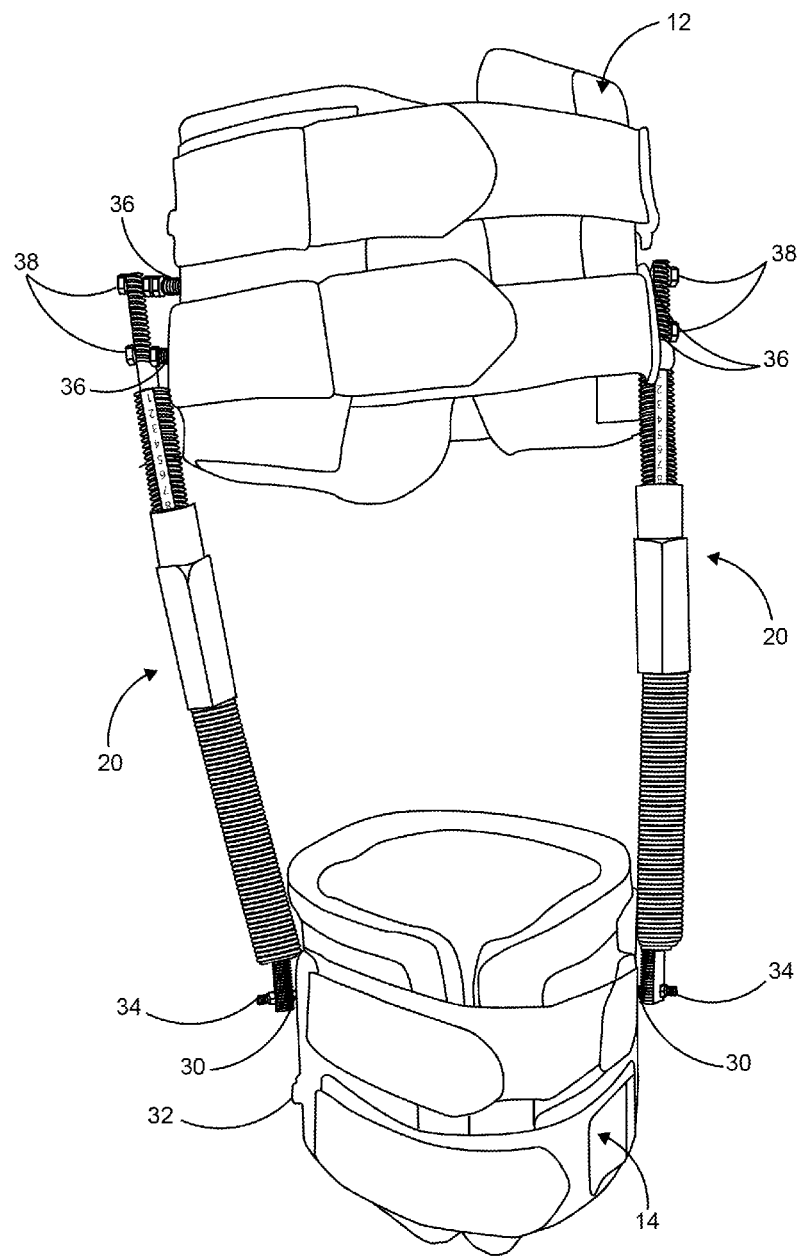
FIG. 19e illustrates the push-push mode of configuration of the present invention applied in the offloader exerting a maximum force.
Figure 19F:
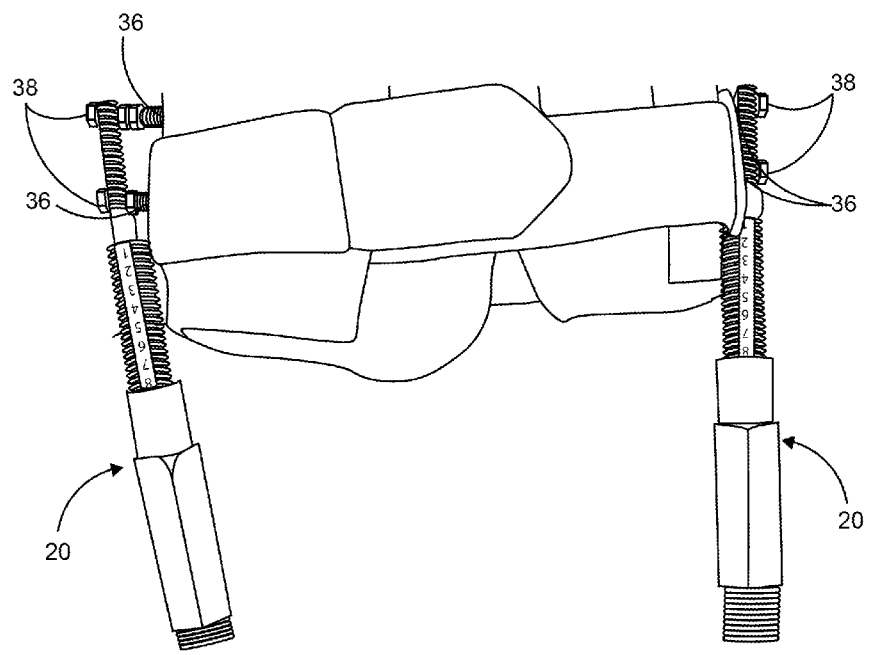
FIG. 19f illustrates a close-up view of the push-push mode of configuration of the present invention applied in the offloader exerting the maximum force.
Figure 20A:
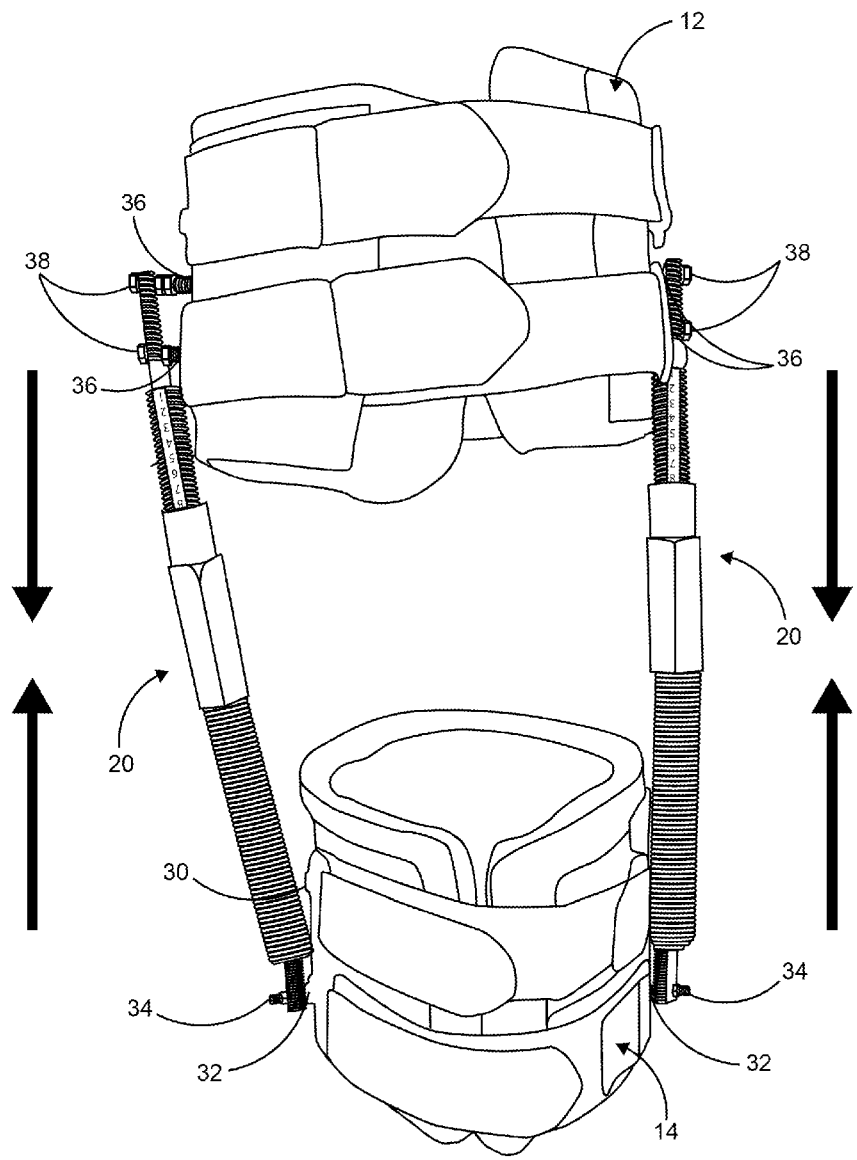
FIG. 20a illustrates a pull-pull mode of configuration of the present invention exerting a minimal force.
Figure 20B:
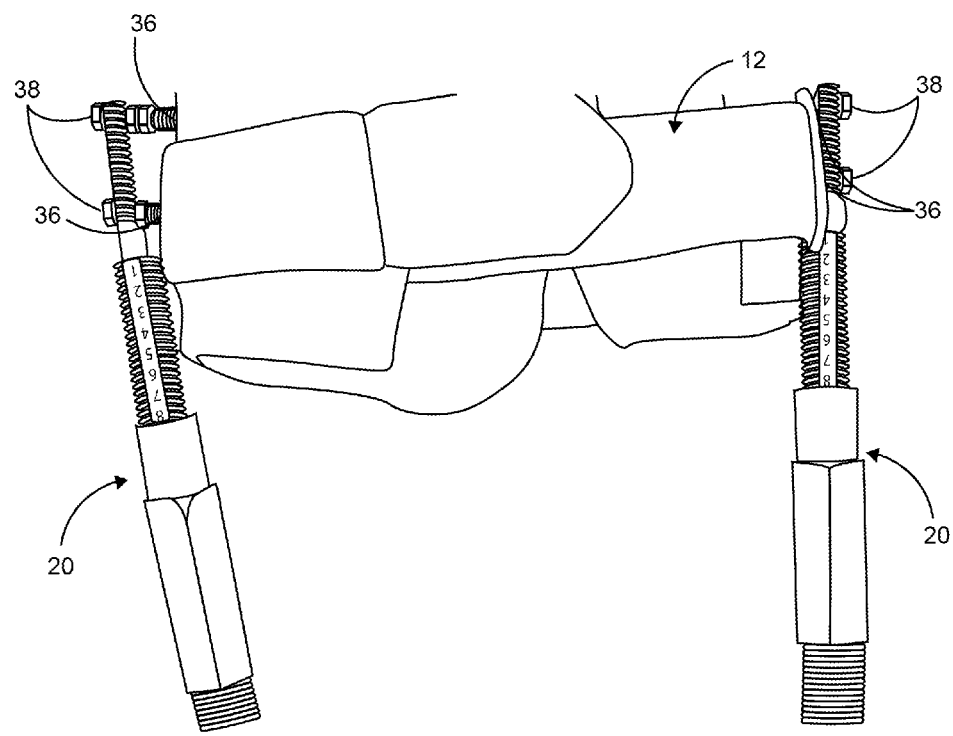
FIG. 20b illustrates a close-up view of the pull-pull mode of configuration of the present invention exerting the minimal force.
Figure 20C:
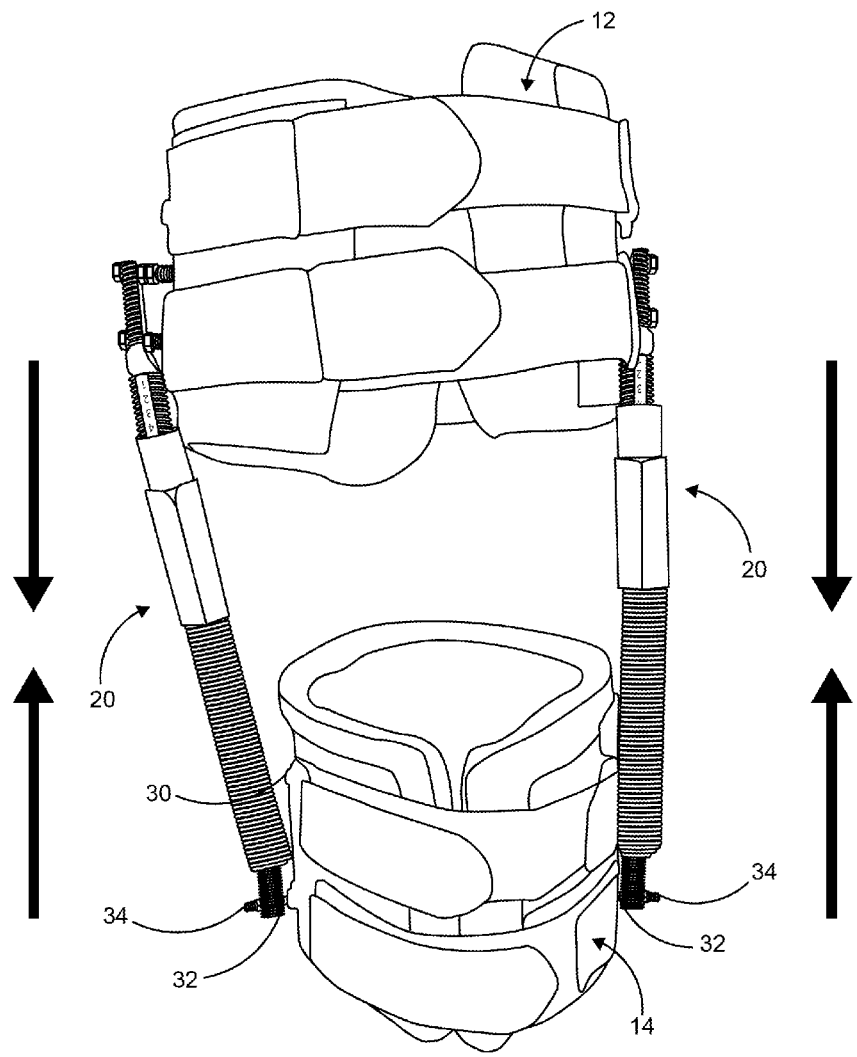
FIG. 20c illustrates the pull-pull mode of configuration of the present invention exerting a medium force.
Figure 20D:
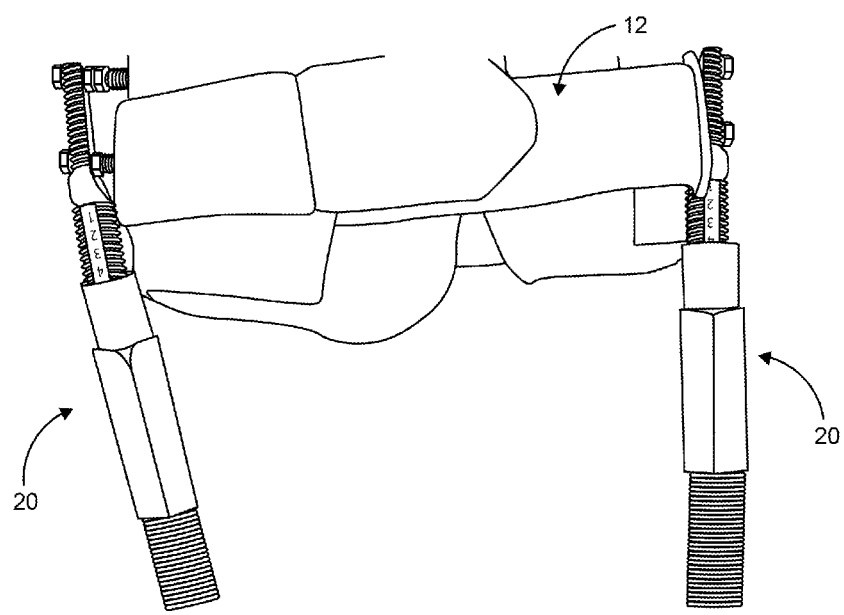
FIG. 20d illustrates a close-up view of the pull-pull mode of configuration of the present invention exerting the medium force.
Figure 20E:
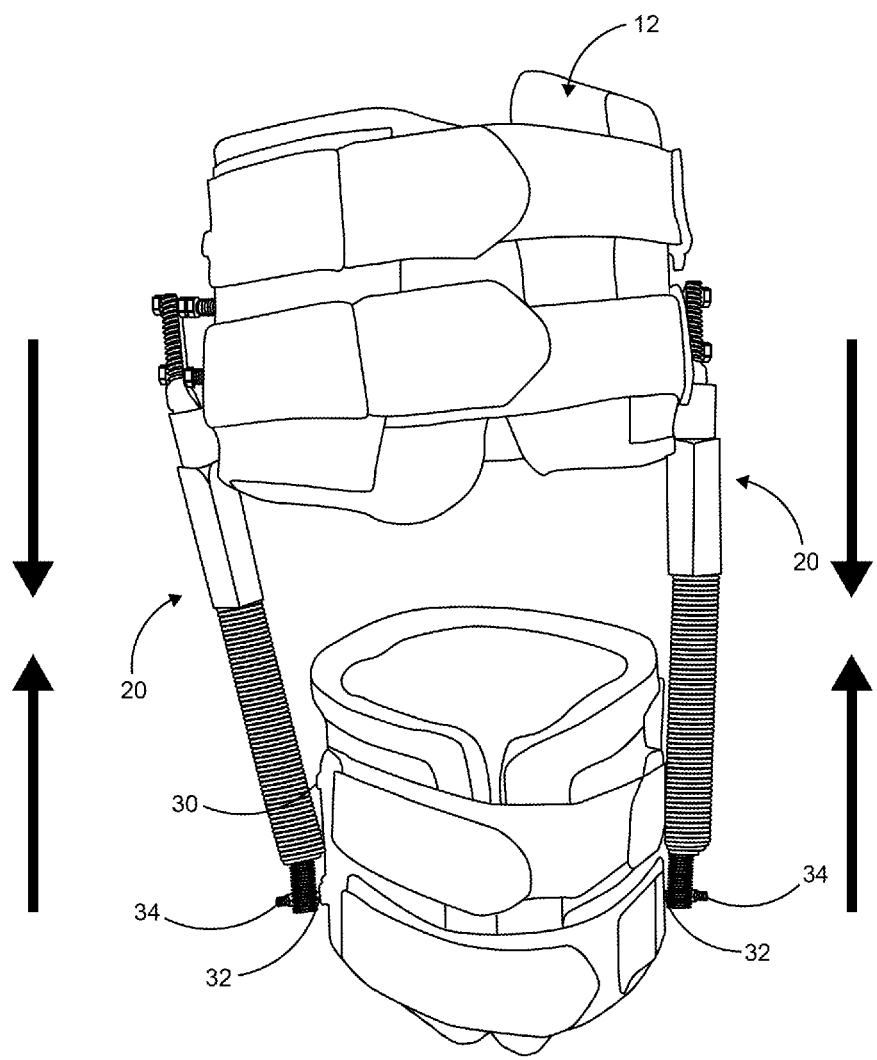
FIG. 20e illustrates the pull-pull mode of configuration of the present invention exerting a maximum force.
Figure 20F:
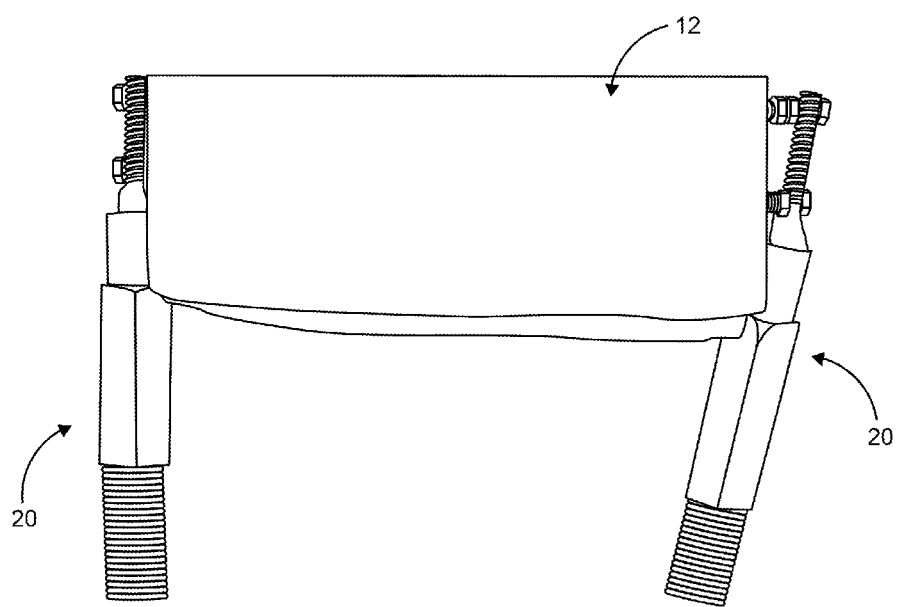
FIG. 20f illustrates a close-up view of the pull-pull mode of configuration of the present invention exerting the maximum force.
Figure 21A:
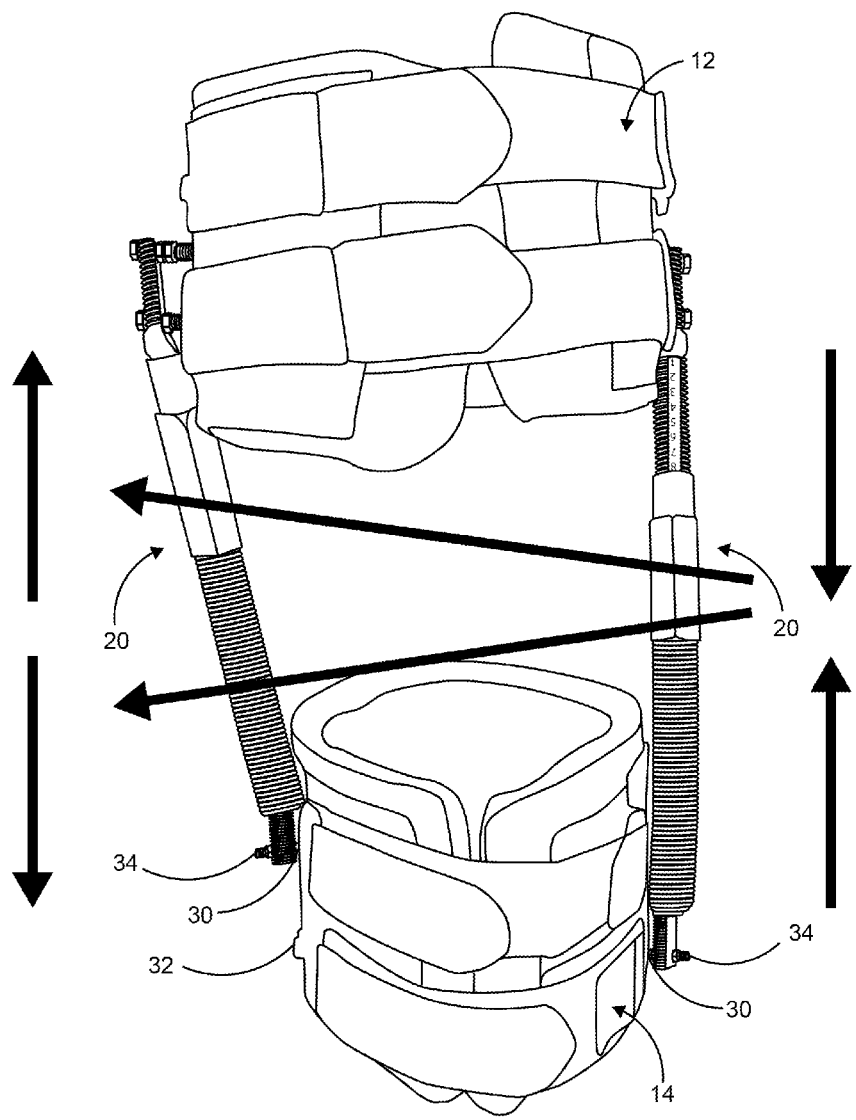
FIG. 21a illustrates a push-pull mode of configuration of the present invention applied in an offloader clamshell exerting a minimal force.
Figure 21B:
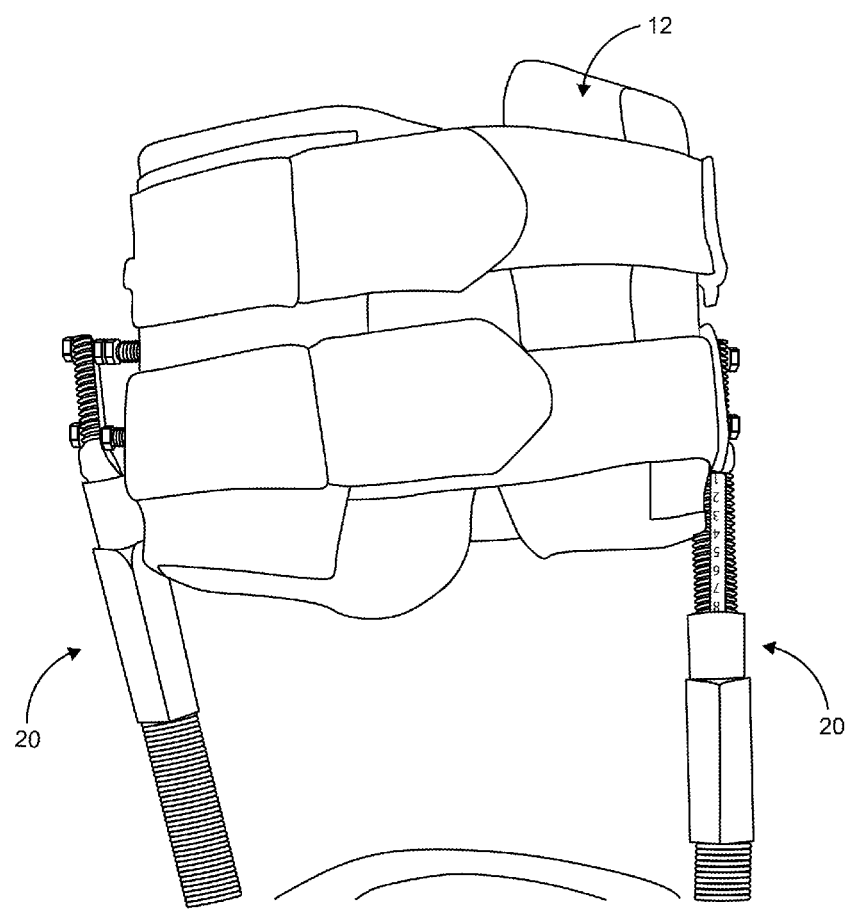
FIG. 21b illustrates a close-up view of the push-pull mode of configuration of the present invention applied in the offloader clamshell exerting the minimal force.
Figure 21C:
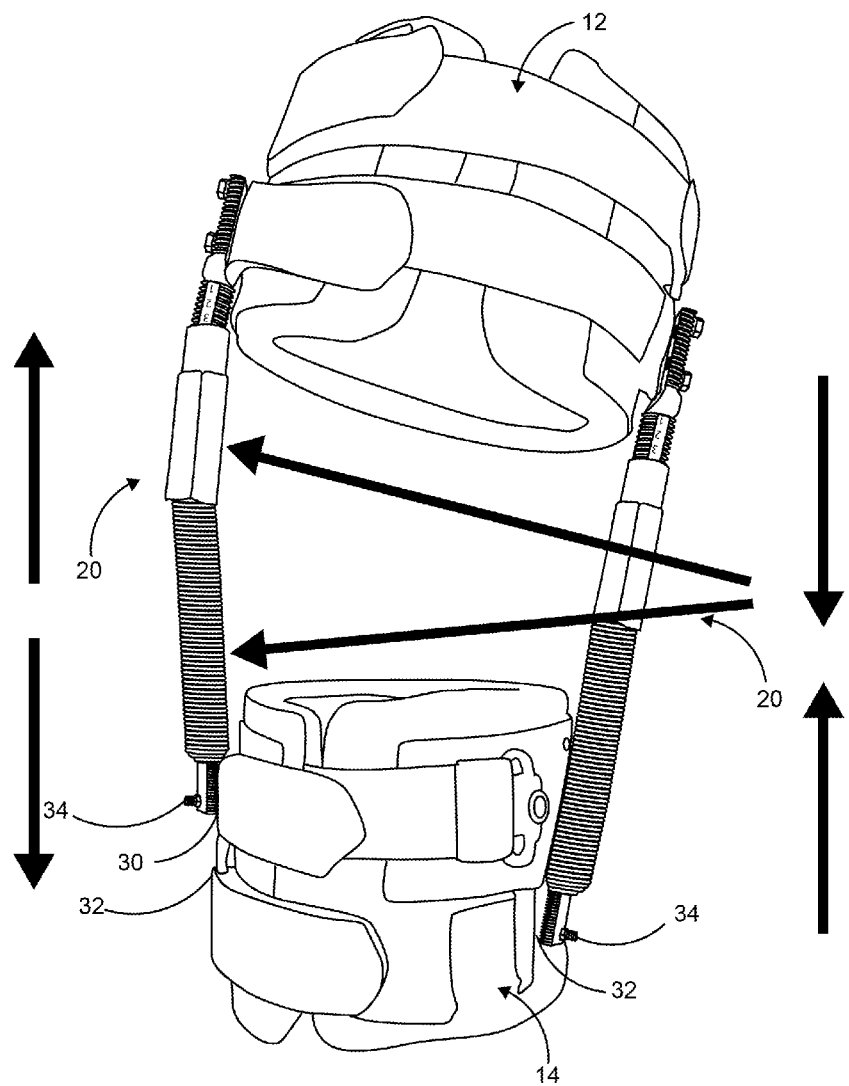
FIG. 21c illustrates a push-pull mode of configuration of the present invention applied in the offloader clamshell with exerting a medium force.
Figure 21D:
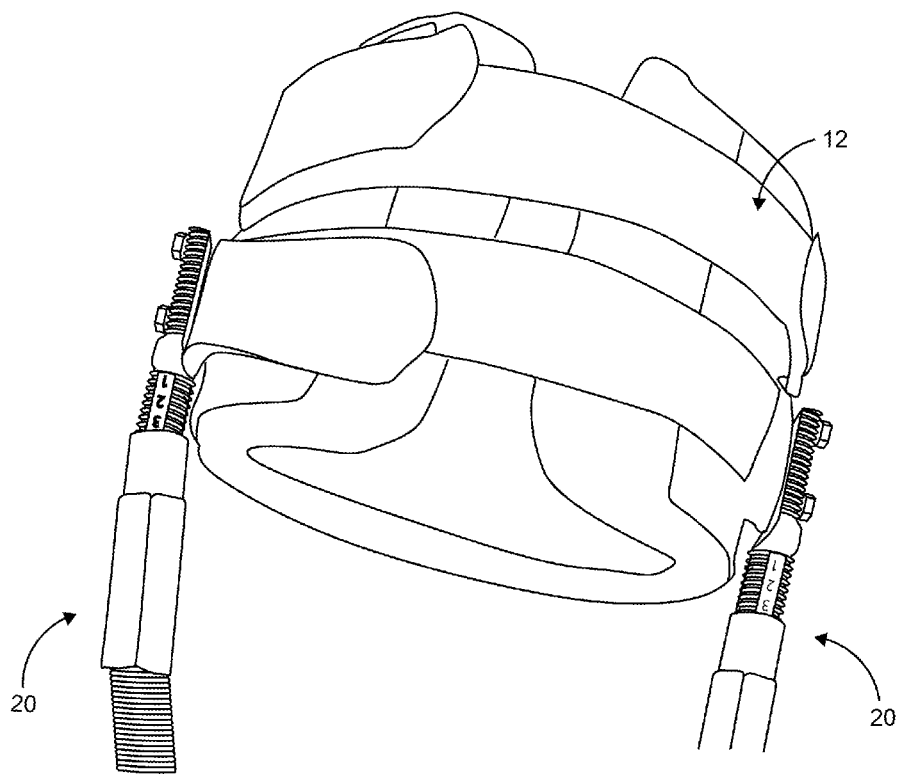
FIG. 21d illustrates a close-up view of the push-pull mode of configuration of the present invention applied in the offloader clamshell exerting the medium force.
Figure 21E:
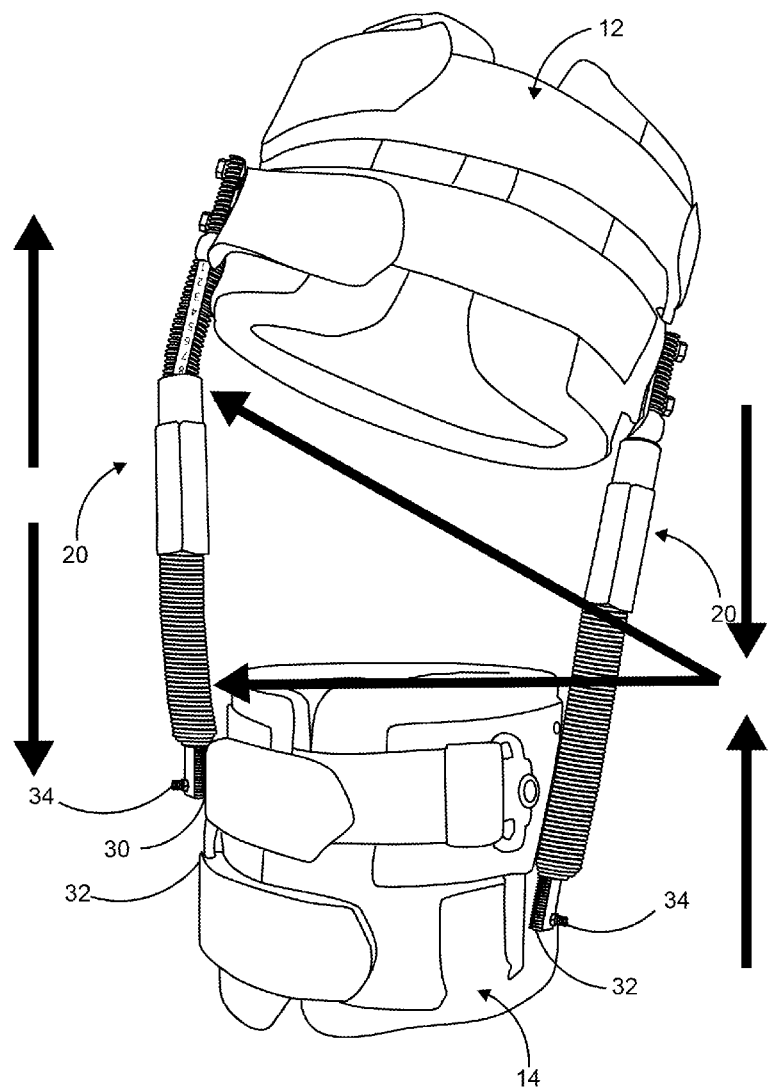
FIG. 21e illustrates a push-pull mode of configuration of the present invention applied in the offloader clamshell exerting a maximum force.
Figure 21F:
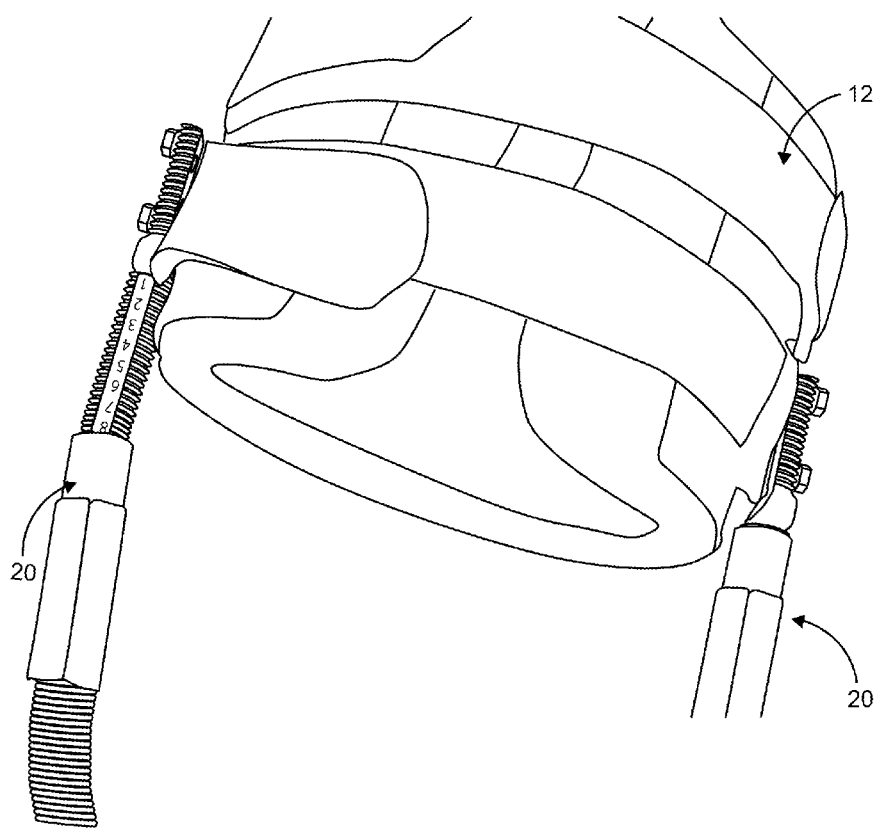
FIG. 21f illustrates a close-up view of the push-pull mode of configuration of the present invention applied in the offloader clamshell exerting the maximum force.

FIG. 18 is a cut away view showing the internals of the at least one spring column assembly 20 in its assembled state.

FIGS. 19a, 19b, 19c, 19d, 19e and 19f illustrate a push-push mode of configuration of the present invention applied in an offloader exerting different levels (minimal, medium and maximum) of force. In push-push mode, each of the spring column assembly 20 is attached to the top notch 30 using the at least one attachment means 34 and the length of the spring column assembly 20 is reduced using the adjustable knob 26 that pushes both sides of the upper cuffs 12 and both sides of the lower cuffs 14 apart. In push-push mode, if both the spring column assembly 20 is lengthened by the same amount, this will result in equal forces on both sides of the upper cuffs 12 as well as the lower cuffs 14. The forces will be in the same direction on both sides of the upper and lower cuffs 12, 14. The direction of the force is outward in both directions from the center point of the spring column 20, as shown by the arrows.

In the push-push mode, the auto-flex knee brace 10 provides relief in both the medial and lateral compartments simultaneously. This is achieved by applying an upward force raising each side of a thigh envelope and applying a lowering force downward against each side of a calf envelope to separate femoral and tibial destructive bone on bone contact.

FIGS. 20a, 20b, 20c, 20d, 20e and 120f illustrate a pull-pull mode of configuration of the present invention exerting different levels (minimal, medium and maximum) of force. In the pull-pull mode, each of the spring column assembly 20 is attached to the bottom notch 32 using the at least one attachment means 34 and the length of the spring column assembly 20 is reduced using the adjustable knob 26 that pulls both sides of the upper cuffs 12 and both sides of the lower cuffs 14 together. In the pull-pull mode, if both the columns 20 are shortened by the same amount, this will result in equal forces on both sides of the upper cuffs 12 and both sides of the lower cuffs 14. The forces will be in the same direction on both sides of the upper and lower cuffs 12, 14. The direction of the force is towards the center of the spring column 20 from both directions, as shown by the arrows.

When the auto-flex knee brace 10 is configured in the pull-pull mode, the brace 10 serves two functions such as the brace 10 can stabilize weak ligaments or acts as a rotational brake, limiting damage to the anterior cruciate ligament during sports activities. In case of stabilizing weak ligaments, the spring column 20 adjustments are used to determine the optimal amount of tightening force and on each side of the knee and in case of rotational brake, the spring column 20 adjustments are used to determine the braking level.

A design that favors the medial joint is useful because knee medial compartments inherently have less cartilage than lateral compartments with the result that 95% of knee joint failures occur in the medial rather than lateral joint. For patients with lax ligaments, configuring the brace 10 in pull-pull mode provides measured knee contractual forces to stabilize the knee. Patients with varus (bow leg) deformity and valgus ("knock knees" deformity), knee crooked (bow legs are bent inward and "knock knees" are bent outward), the multi-axial, flexible spring column 20 compensates for the misshapen knee curve and provides full support. Obese patients are accommodated because the patient's weight is supported by incompressible steel springs of the auto-flex knee brace 10. Also, the upper and lower thigh cuffs 12, 14 offer generous circumferential coverage and thus prevent thigh and calf intravascular injuries as well as offer low pound force by area in distributing the load.

FIGS. 21a, 21b, 21c, 21d, 21e and 21f illustrate a push-pull mode of configuration of the present invention applied in an offloader clamshell exerting different levels (minimal, medium and maximum) of force. In the push-pull mode, one of the spring column assembly 20 is attached to the top notch 30 and another spring column assembly 20 is attached to the bottom notch 32 using the at least one attachment means 34 and the length of the spring column assembly 20 attached to the top notch 30 is increased to achieve a push on one side of the cuffs 12, 14 and the length of the spring column assembly 20 attached to the top notch 30 is reduced to achieve a pull on other side of the cuffs 12, 14 using the adjustable knob 26. In push-pull mode, if the shorter column 20 is lengthened by the same amount that the longer column 20 is shortened, this will result in equal forces on both sides of the upper cuffs 12 and both sides of the lower cuffs 14. The forces on the left ("push") side of the brace 10 will be outward from the center of the spring columns 20 in both directions and the forces on right ("pull") side of the brace 10 will be towards the center of the spring columns 20, as shown by the arrows.

In the push-pull mode, the angle of the femur can be further increased by configuring each of the spring column assembly 20 to exert their respective forces in opposite directions. This is accomplished by mounting the spring columns 20 at different relative positions between the upper and lower thigh cuffs 12, 14.

Figure 22A:
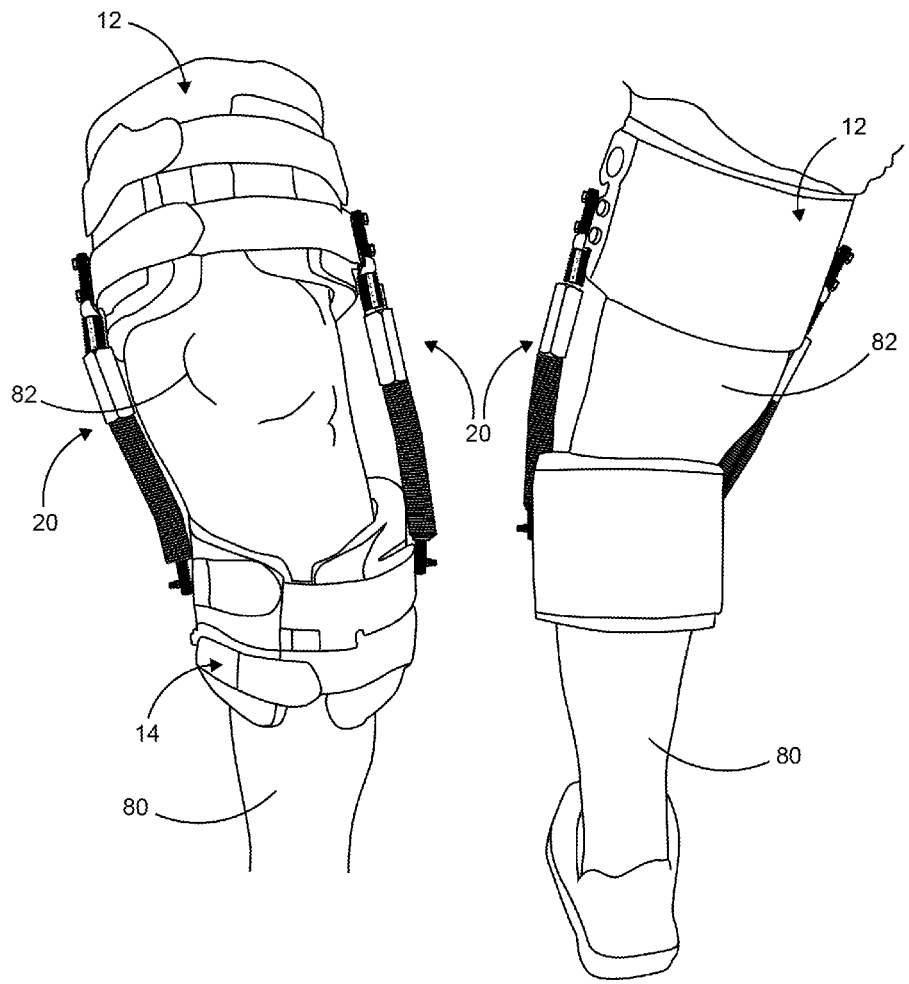
FIG. 22a illustrates a front view and a rear view of the present invention worn over a leg of a user configured in the push-push mode applied in the offloader brace.
Figure 22B:
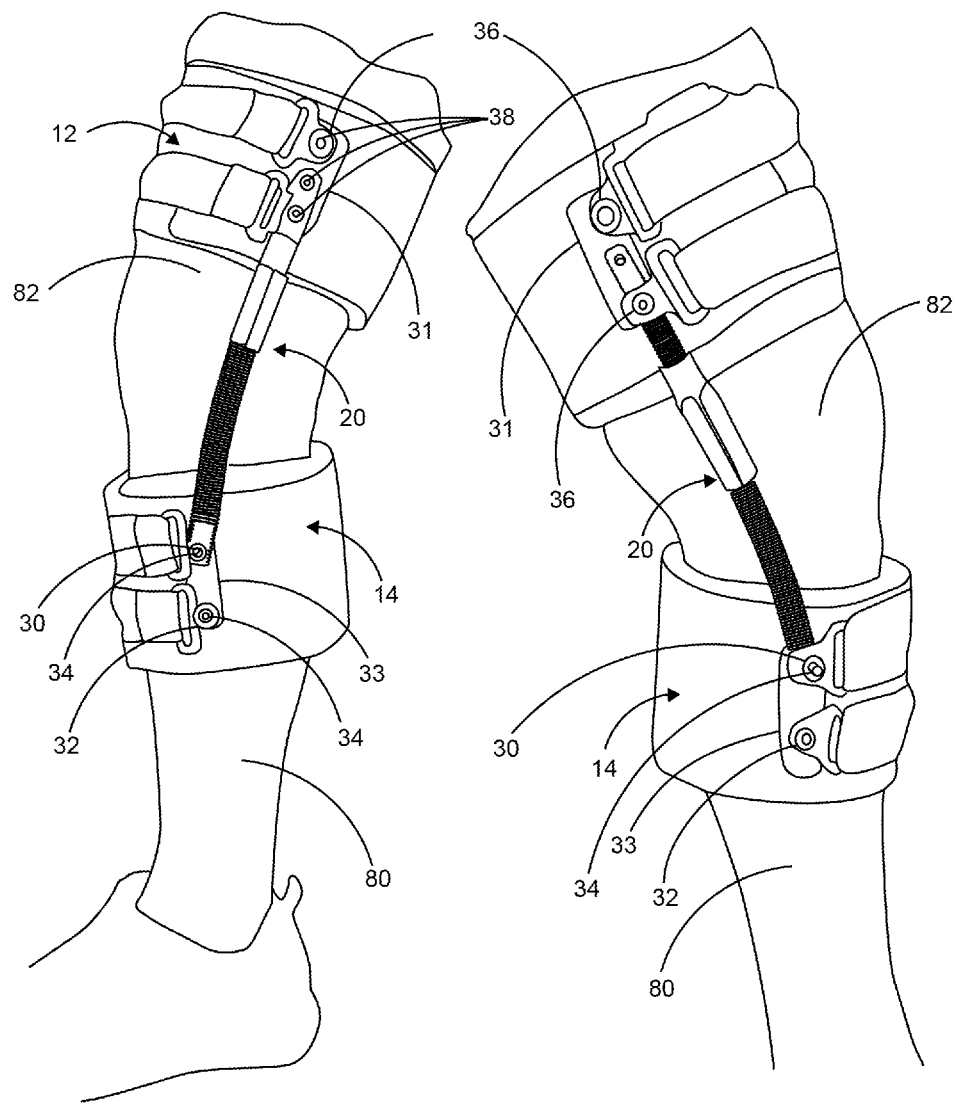
FIG. 22b illustrates a left side view and a right side view of the present invention worn over the leg of the user configured in the push-push mode applied in the offloader brace.

FIGS. 22a and 22b illustrate different views of the auto-flex knee brace 10 worn over a leg of a user 80 configured in the push-push mode applied in the offloader brace. The lower thigh cuff 14 includes the slot 33 having the top notch 30 and the bottom notch 32. The lower cuff connection rod 24 slides through the slot 33 and connects to the top notch 30 or the bottom notch 32 through the at least one screw aperture 74 utilizing at least one attachment means 34. Similarly, the upper thigh cuff 12 includes the slot 31 having the plurality of notches 36. The upper cuff connection rod 28 slides through the slot 31 and connects to the plurality of notches 36 through the plurality of screw apertures 76 utilizing at least one attachment means 38.

Figure 23:
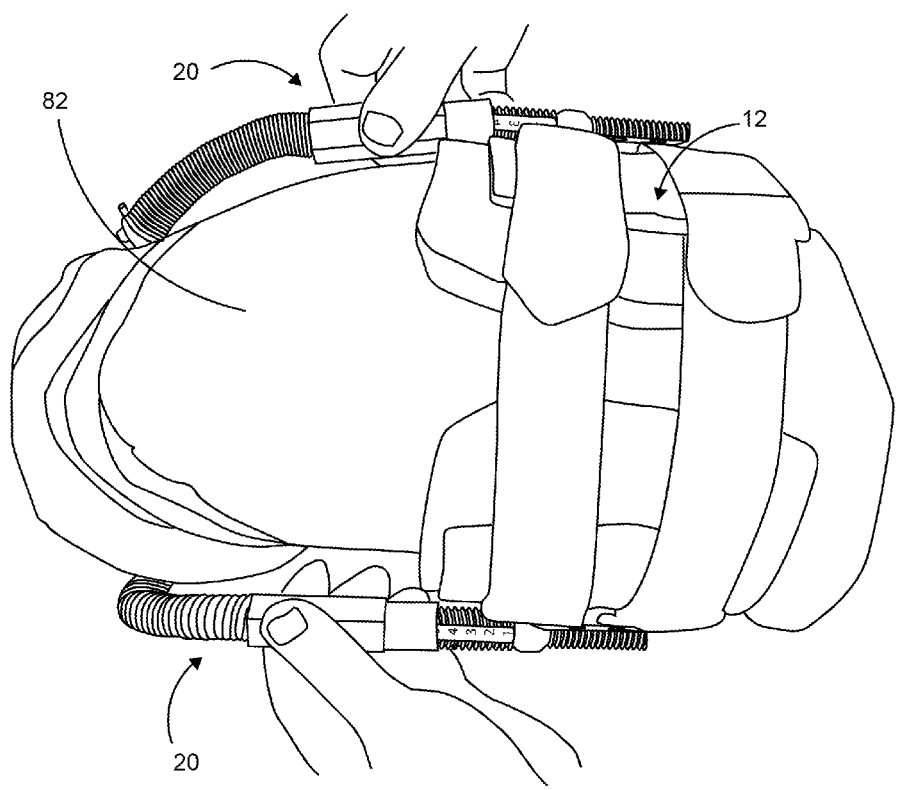
FIG. 23 illustrates the configuration of the present invention to achieve the push-push mode in the offloader brace.

FIG. 23 illustrates the configuration of the auto-flex knee brace 10 to achieve the push-push mode in the offloader brace.

The spring-based design of the auto-flex knee brace 10 offers benefits over conventional off-loader braces. The auto-flex knee brace 10 in an off-loader brace action is bi-compartmental rather than uni-compartmental resulting in condylar separation in both the medial and lateral knee compartments simultaneously. Condylar separation reduces articular bone scraping which inhibits cartilage cell procreation and provides normal replacement of femoral cartilage and tibial menisci through natural or artificial seeding supplements. The condylar separation also occurs when the knee 82 is in full flexion at rest, e.g. in bed or in a recliner. This reduces the "pre-tensioned loading" that the knee 82 normally experiences at this time, i.e. the ligaments holding the bones against each other, creating articular bone contact. The problem of pre-tensioned loading is of particular concern when articular knee bones shift sleeping positions frequently and irritate compartmental menisci. Using the spring columns 20 set in the push-push mode, the auto-flex knee brace 10 supports daily, nocturnal and programmed ligament activity.

In push-pull mode, the spring columns together exert an angular force outward on the femur and shinbones, resulting in a pivot that closes the lateral gap and opens the medial gap. That is, the lateral gap is reduced and the medial gap is increased from what they would be in push-push mode. The result is a clamshell effect whereby the medial joint is able to shift some of the extra gap in the lateral joint. That is, the pull and push springs attached to the upper and lower thigh cuffs 12, 14 provide the power to activate what is effectively a knee joint clamshell assembly.

Figure 24A:
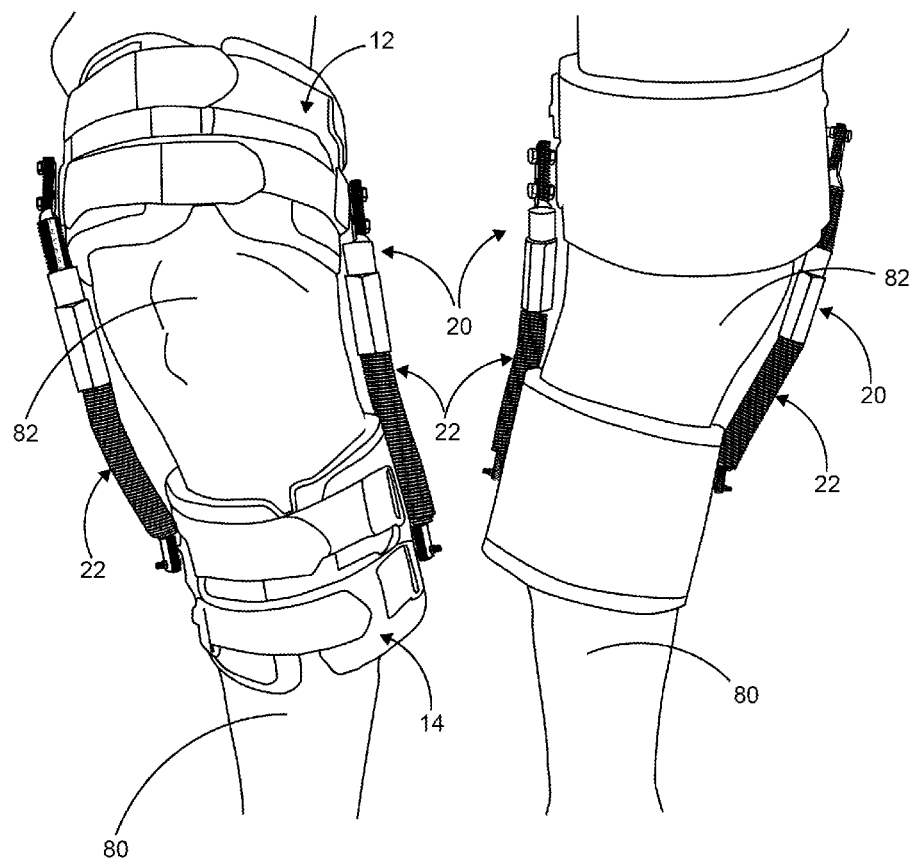
FIG. 24a illustrates a front view and a rear view of the present invention worn over the leg of the user configured in the push-pull mode applied in the offloader clamshell.
Figure 24B:
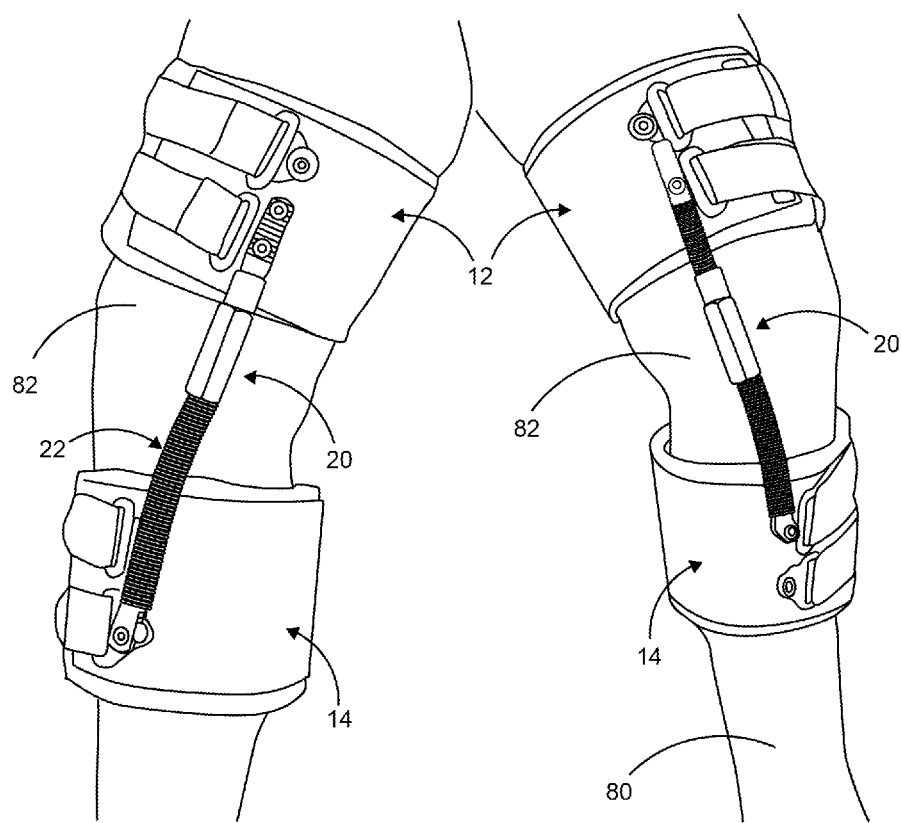
FIG. 24b illustrates a left side view and a right side view of the present invention worn over the leg of the user configured in the push-pull mode applied in the offloader clamshell.
Figure 25A:
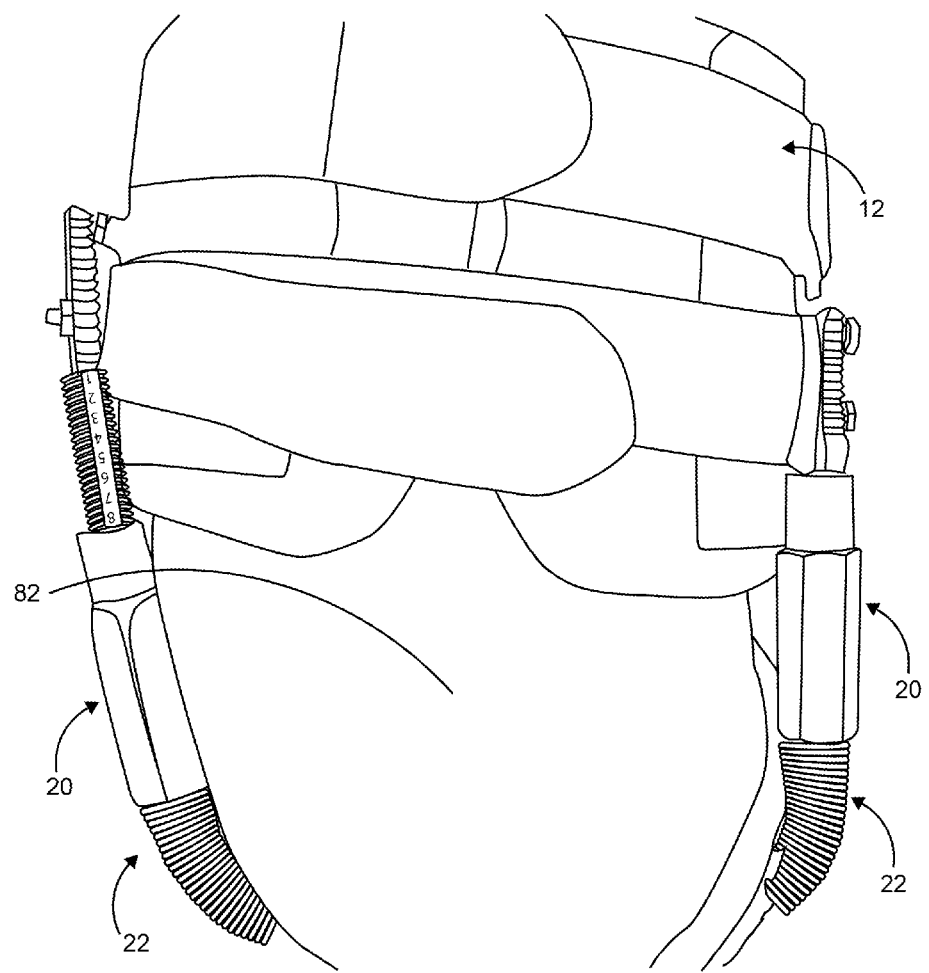
FIG. 25a illustrates a top view of the present invention worn on a bended knee configured in the push-pull mode applied in the offloader clamshell.
Figure 25B:
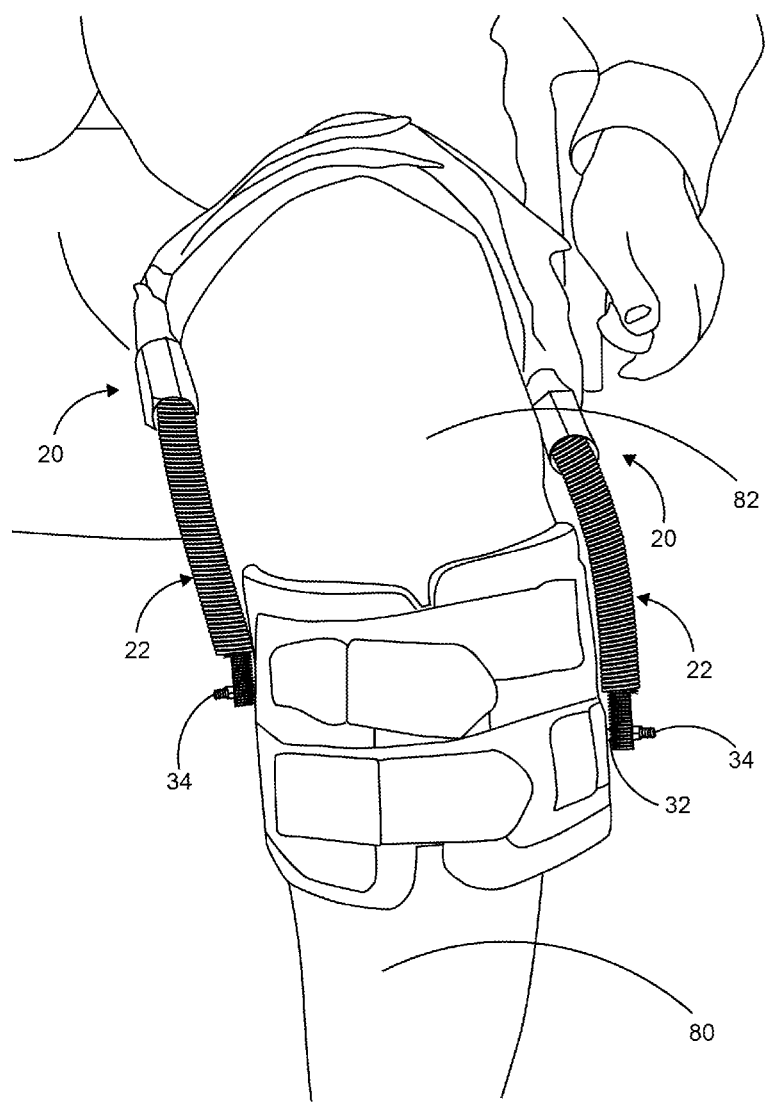
FIG. 25b illustrates a front view of the present invention worn on the bended knee configured in the push-pull mode applied in the offloader clamshell.
Figure 25C:
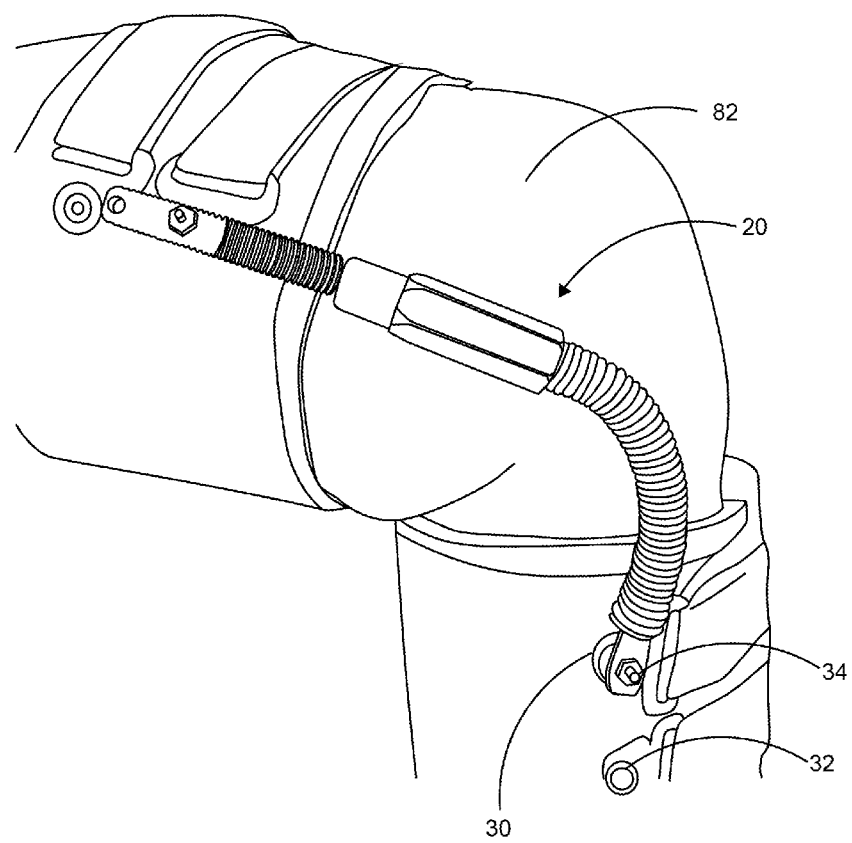
FIG. 25c illustrates a right side view of the present invention worn on the bended knee configured in the push-pull mode applied in the offloader clamshell.
Figure 25D:
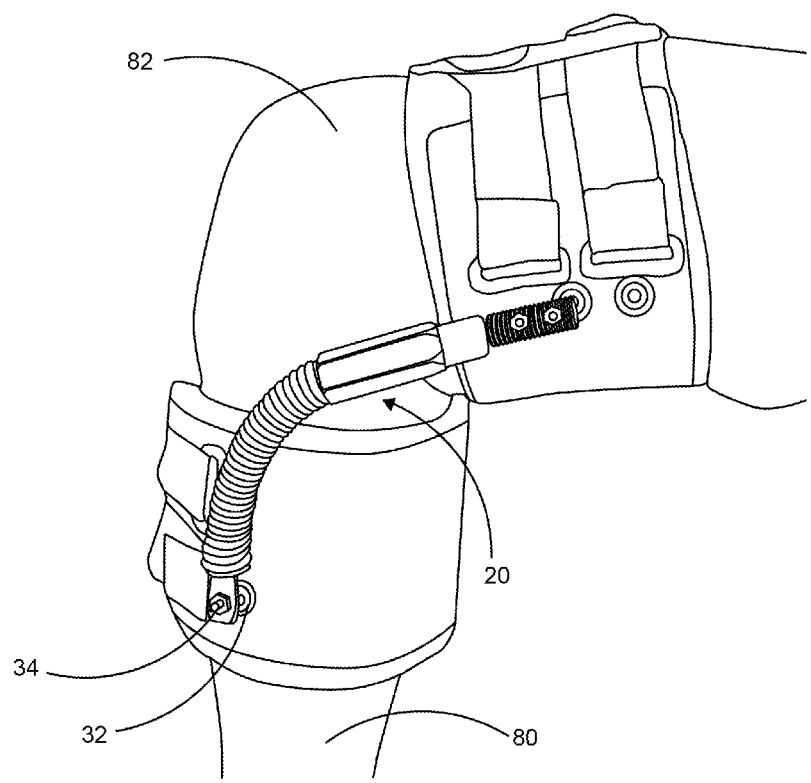
FIG. 25d illustrates a left side view of the present invention worn on the bended knee configured in the push-pull mode applied in the offloader clamshell.
Figure 26:
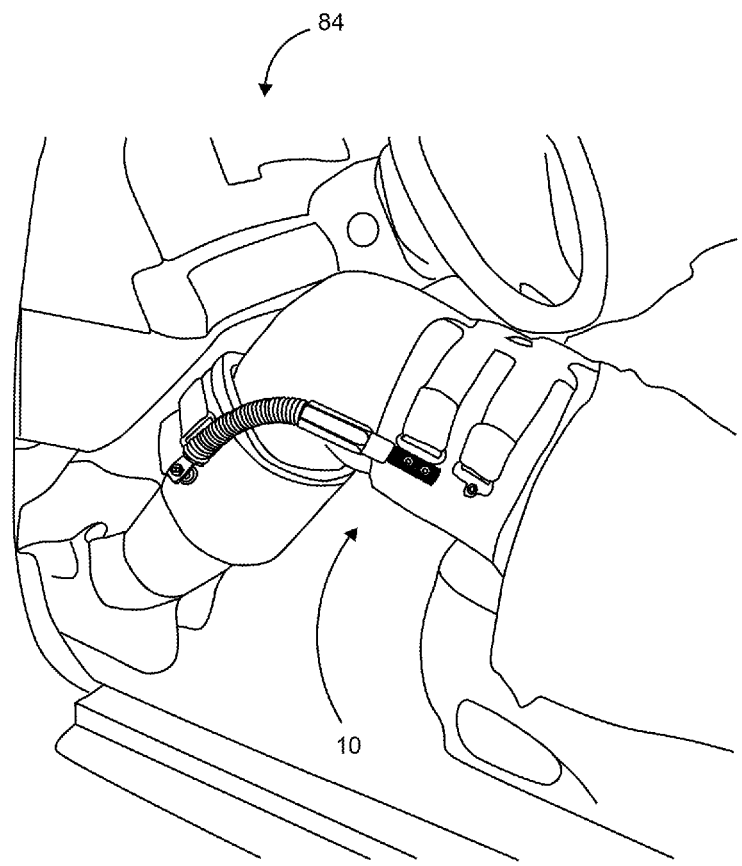
FIG. 26 shows the user worn with the auto-flex knee brace getting into a car.

FIGS. 24a and 24b illustrate different views of the auto-flex knee brace 10 worn over a leg of a user 80 configured in the push-pull mode applied in the offloader clamshell. The spring column assembly 20 curves to support knee deformities. FIGS. 25a, 25b, 25c and 25d illustrate different views of the auto-flex knee brace 10 worn on a bended knee 82 configured in the push-pull mode applied in the offloader clamshell. In the push-pull (offloader clamshell) mode, the forces have a clamshell offloading affect, pulling together one side and pushing apart the other. The extension spring 22 on the left bends at a lower place along its length than the extension spring 22 on the right. This illustrates the "floating hinge" action. FIG. 26 shows the user wearing the auto-flex knee brace 10 getting into a car 84.

Figure 27:
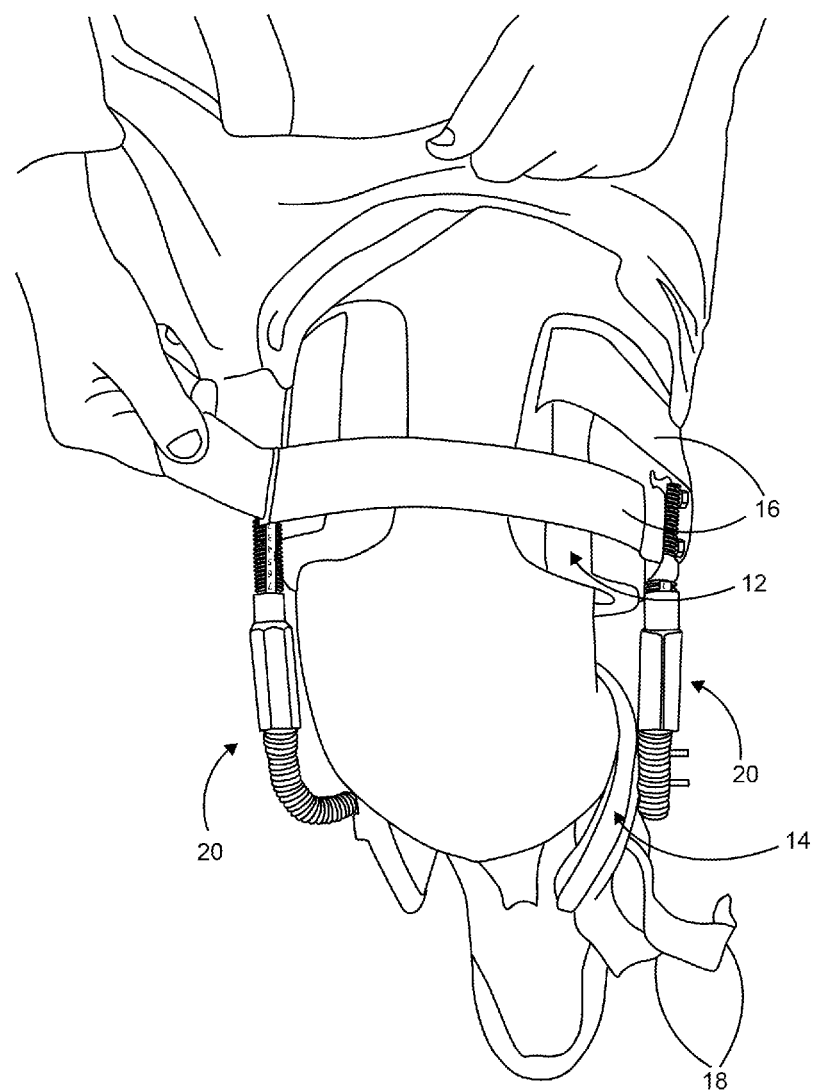
FIG. 27 is an illustration of securing a first strap means over the upper thigh cuff that worn over the knee.

FIG. 27 is an illustration of securing the first strap means 16 over the upper thigh cuff 12 that is worn over the knee 82. The first strap means 16 and the second strap means 18 is tied around the upper thigh cuff 12 and the lower thigh cuff 14 using a Velcro means. The auto-flex knee brace 10 is attached to the leg 80 by placing the cuffs 12, 14 around the thigh and calf and pulling tight Velcro straps attached to the cuffs 12, 14.

Figure 28:
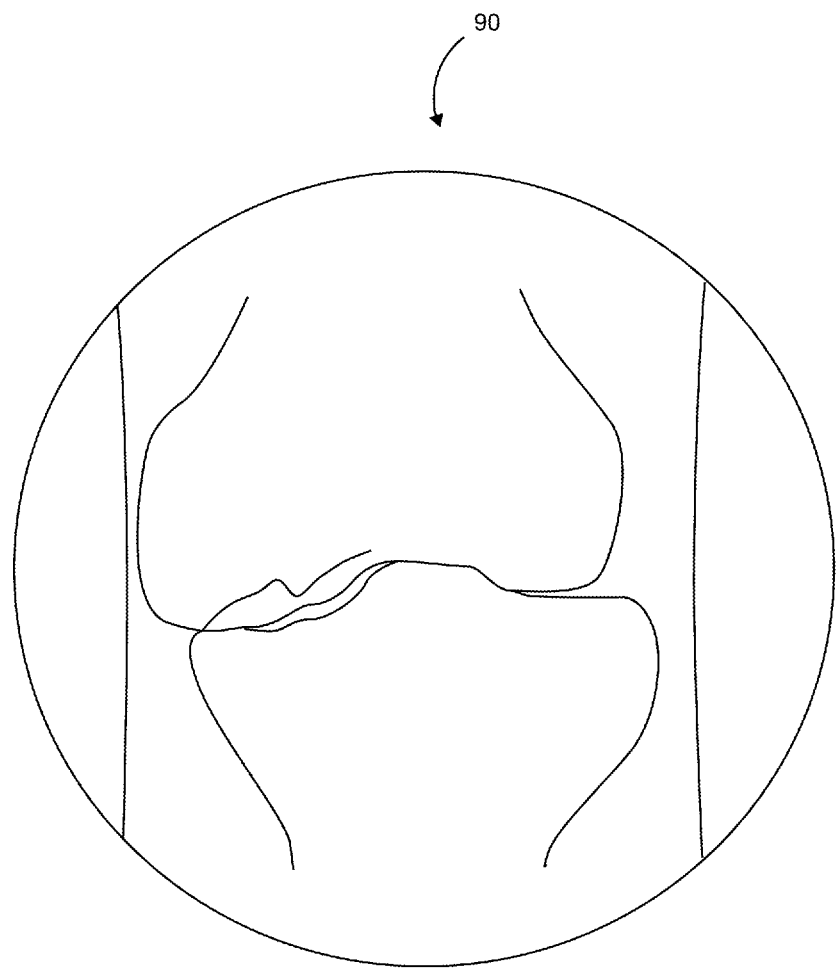
FIG. 28 schematically illustrates an X-ray image of a weight bearing left knee of an osteoarthritis patient.

FIG. 28 schematically illustrates an X-ray image 90 of a weight bearing left knee 82 of an osteoarthritis patient. The patient is standing and is an 86-year old patient who is 6'3" and weighs 270 lbs. An exceptionally small gap in the medial joint on the left side of knee 82 is viewed.

Figure 29:
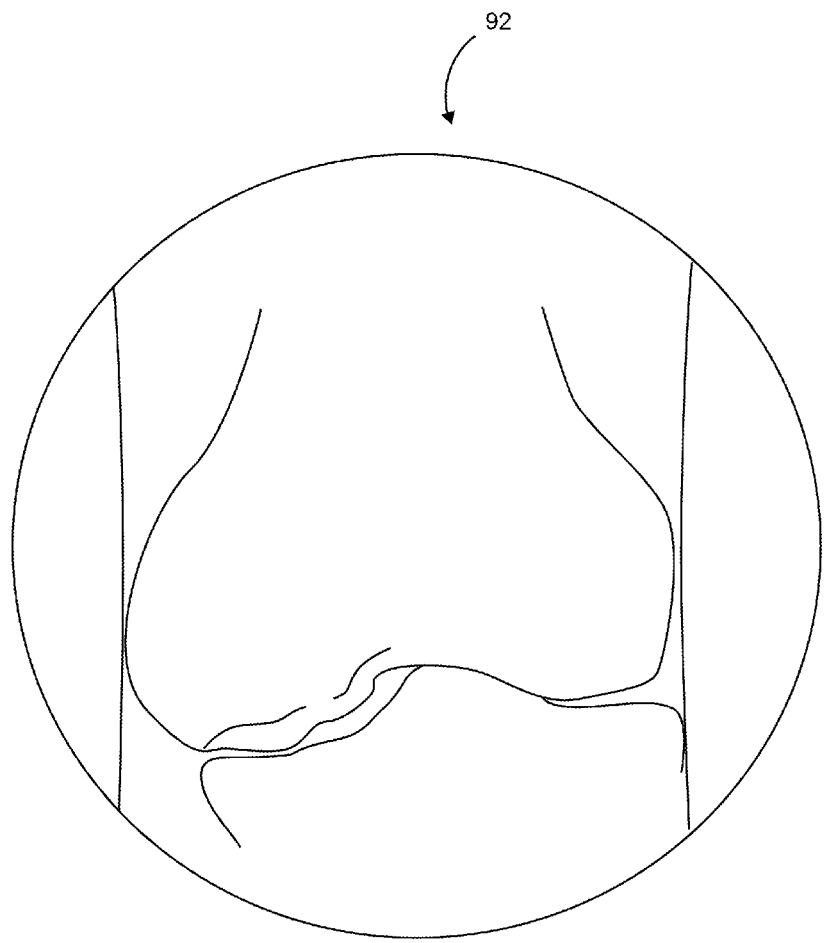
FIG. 29 illustrates the schematic X-ray image shown in FIG. 28 with the use of the present invention configured in the push-pull offloader clamshell mode exerting the maximum force.
Figure 30:
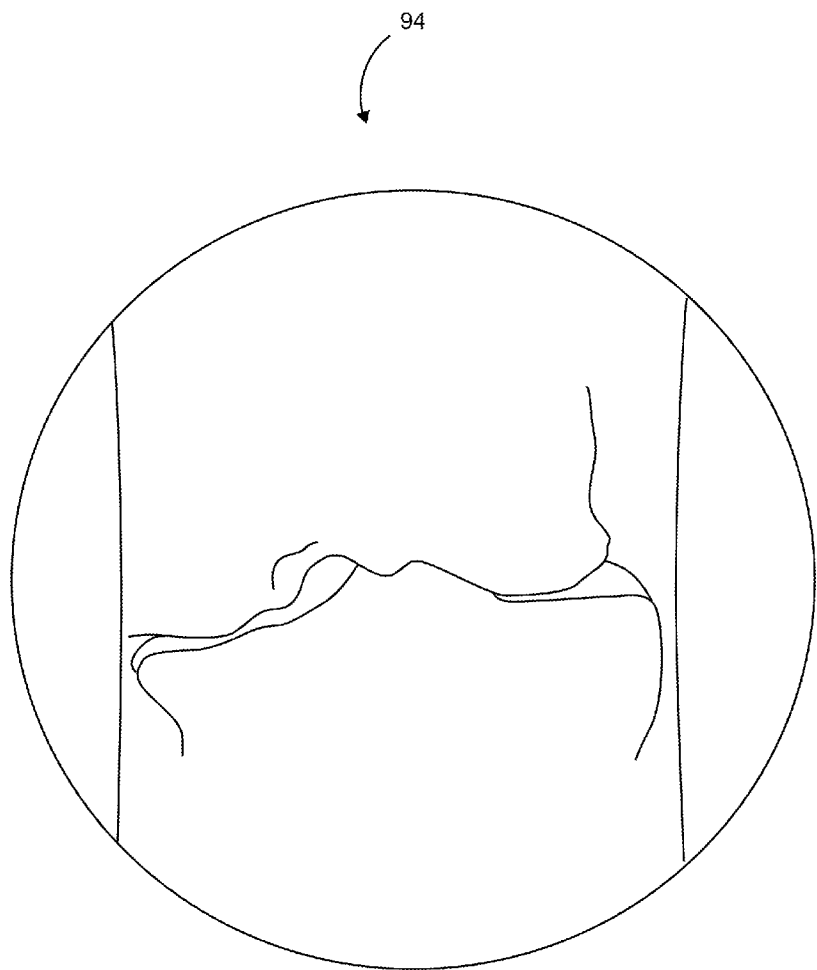
FIG. 30 illustrates the schematic X-ray image shown in FIG. 29 in which the leg of the user is lifted off the ground.

FIG. 29 illustrates the schematic X-ray image 92 shown in FIG. 28 with the use of the present invention configured in the push-pull offloader clamshell mode exerting the maximum force. Here, an increase in the gap in the medial joint can be viewed. FIG. 30 illustrates the schematic X-ray image 94 shown in FIG. 29 in which the leg of the user 80 is lifted off the ground (non-weight bearing). Here, even greater increase in the gap in the medial joint can be viewed.

Figure 31:
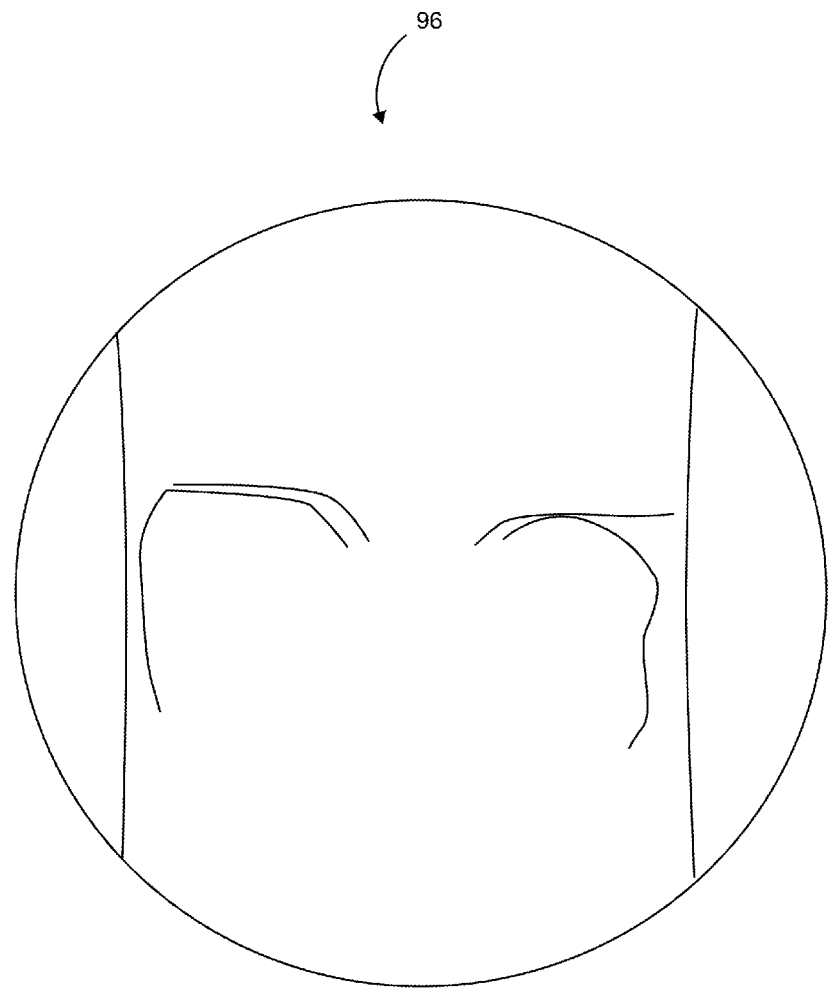
FIG. 31 illustrates the schematic X-ray image shown in FIG. 29 with the use of the present invention configured in the pull-pull mode.
Figure 32A:
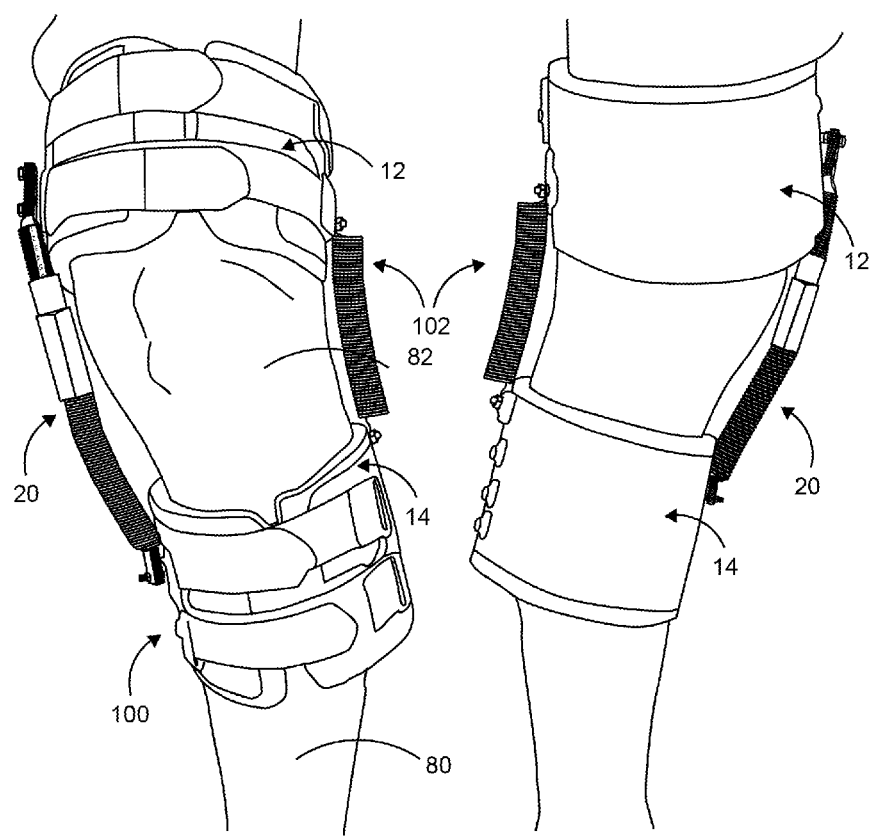
FIG. 32a illustrates a front view and a rear view of one embodiment of the present invention.
Figure 32B:
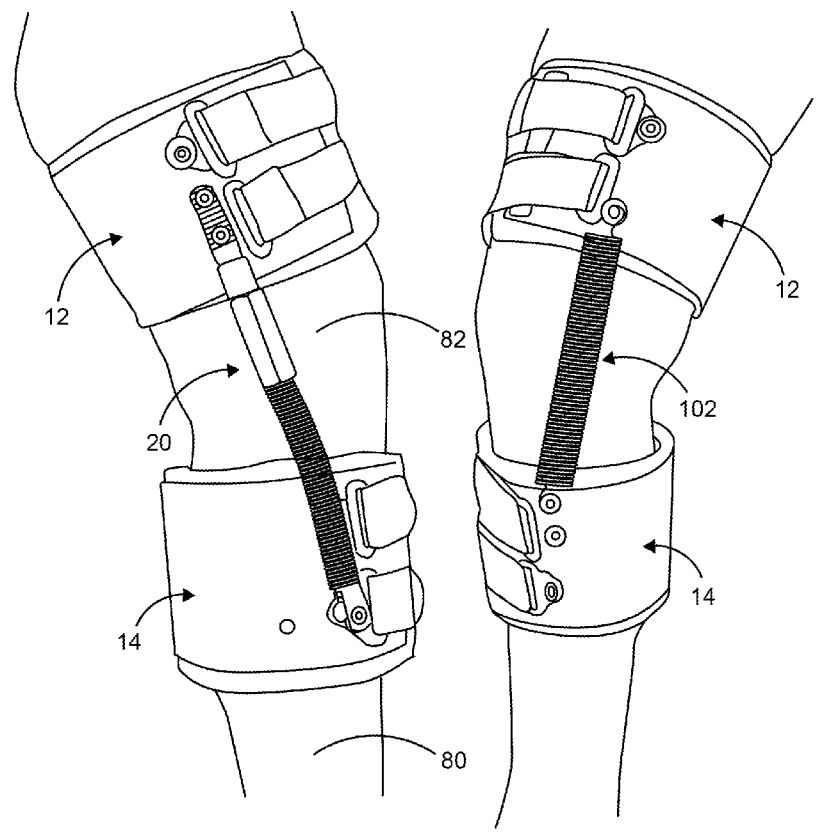
Figure 32C:
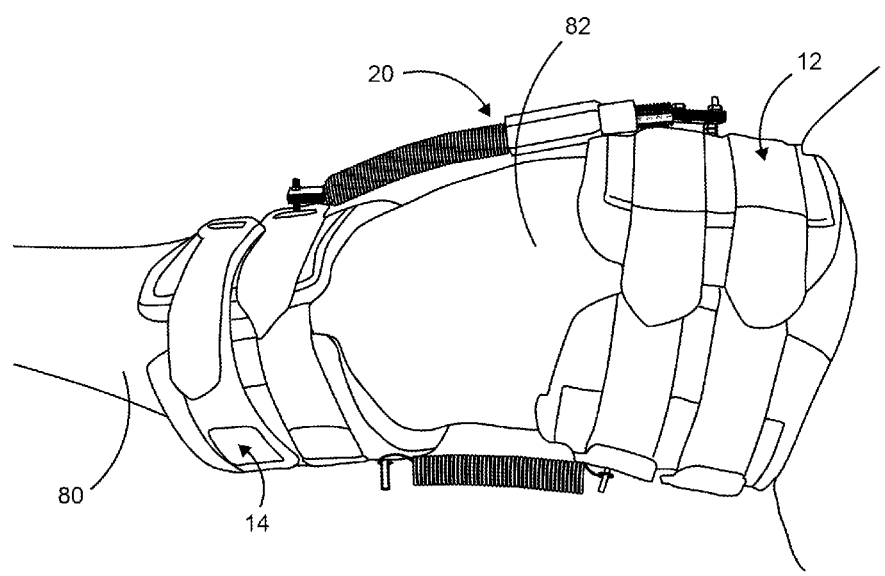
FIG. 32c illustrates a top view of the embodiment shown in the FIG. 32a worn over an extended leg of the user.
Figure 32D:
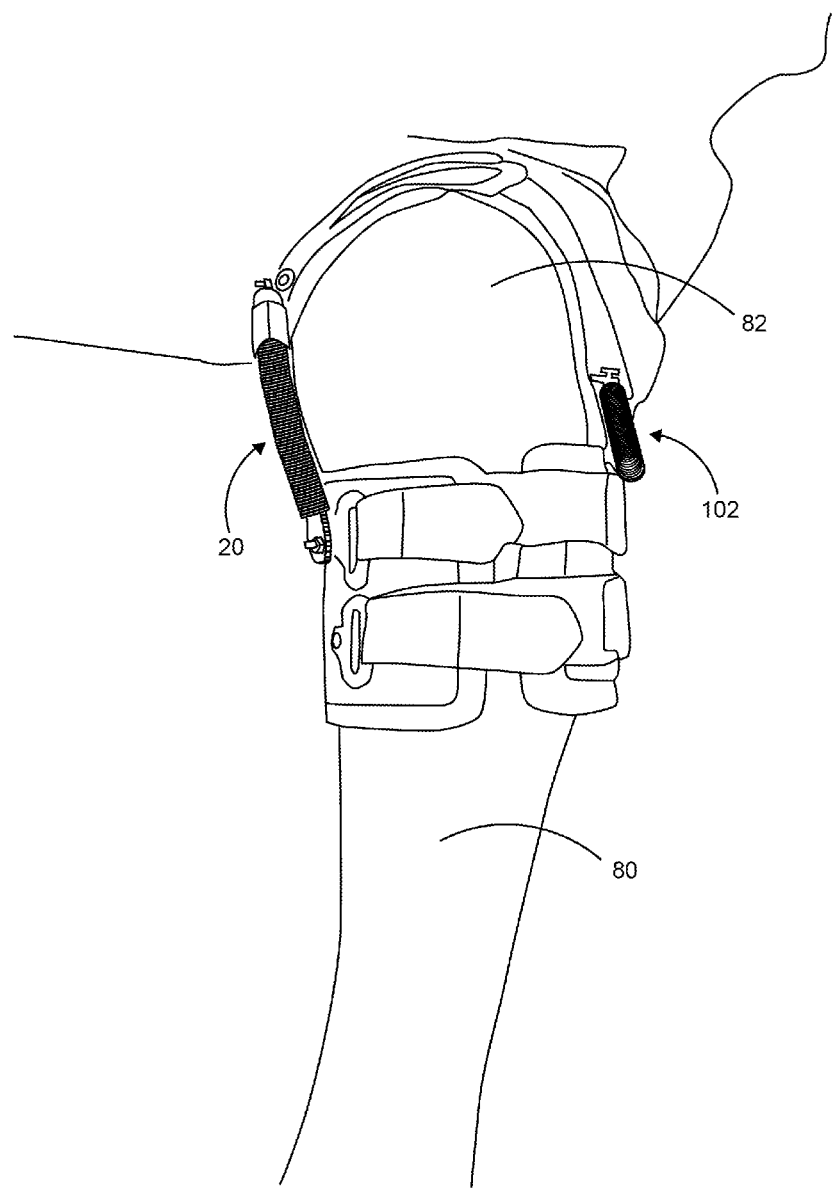
FIG. 32d illustrates a front view of the embodiment shown in the FIG. 32a worn on the bended knee.
Figure 32E:
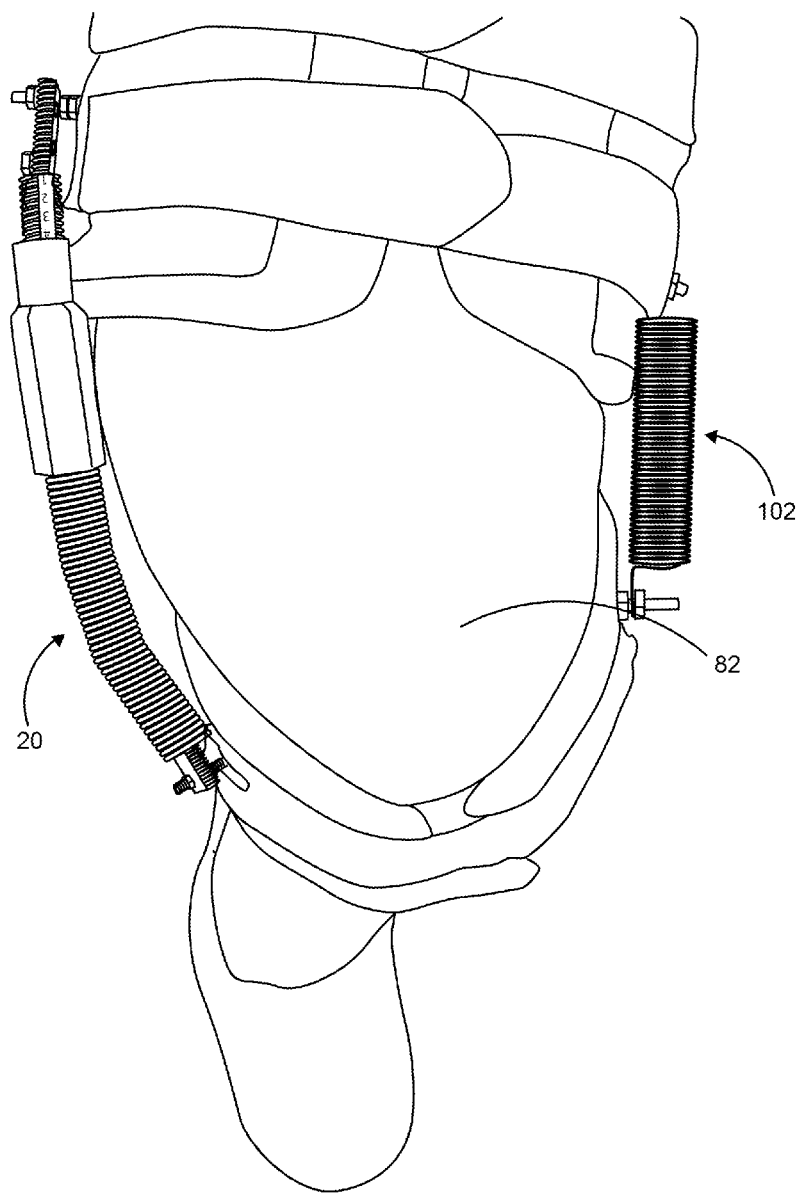
FIG. 32e illustrates a top view of the embodiment shown in the FIG. 32a worn on the bended knee.
Figure 32F:
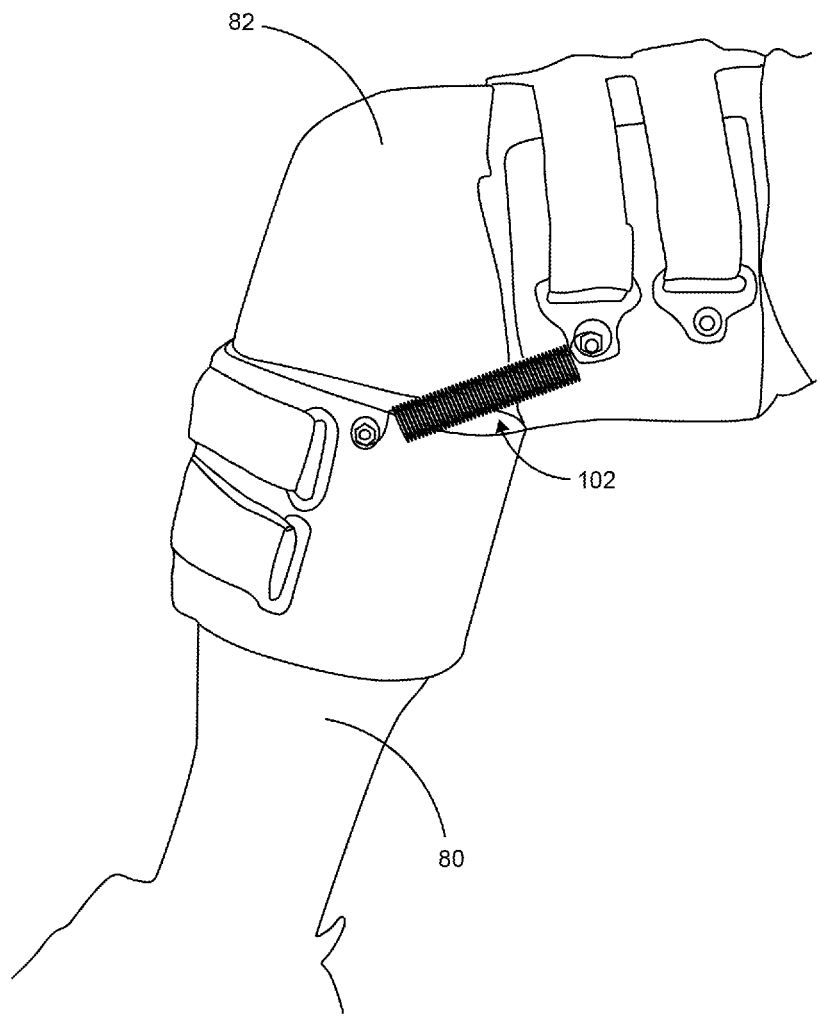
FIG. 32f illustrates a left side view of the embodiment shown in the FIG. 32a worn on the bended knee.

FIG. 31 illustrates the schematic X-ray image 96 shown in FIG. 29 with the use of the present invention configured in the pull-pull mode. Here, the auto-flex knee brace 10 dials set to 3-3 and a significant decrease in the gap in the medial joint can be viewed.

The auto-flex knee brace 10 can be used in all four of the common knee brace applications. Offloader is the primary application of the auto-flex knee brace 10. Its spring-based design offers the following benefits over conventional off-loader braces. The auto-flex knee brace 10 off-loader brace action is bi-compartmental rather than uni-compartmental resulting in condylar separation in both the medial and lateral knee compartments simultaneously. Off-loading in the current state-of-the-art occurs only momentarily (i.e. during heel strike). Functional mode is the other application of the auto-flex knee brace 10. The auto-flex knee brace 10 can be used to stabilize weak knees. The spring columns 20 support heavy loads and keep the knee in place. Lax ligaments can be compensated for by tightening (shortening) the spring columns and increasing the pressures on the knee compartments. The auto-flex knee brace 10 can also be used in rehabilitative mode. It supports the knee during recovery. It also prevents the knee from twisting using the rotational resistance feature.

The prophylactic mode is yet another application. When a brace is subjected to lateral stress (such as a skiing accident), it is important that a knee brace offers high rotational resistance to keep the knee from twisting. However, if the resistance is too high, then when a quick snapping motion occurs, many knee braces experience slippage in the cuffs attached to the upper and lower legs. The result is that the braking action of the brace is greatly reduced. On the other hand, the present invention suffers less from this problem because its stiff springs do not completely resist the rotational motion. That is, they have "gradual give". This means that much of the energy in the snapping action is dissipated in the springs before the metal cuffs have a chance to slip. The result is that the knee rotates only slightly and slowly, limiting damage to the anterior cruciate ligament (ACL). It is estimated that 70 percent of all ACL injuries are non-contact in nature, i.e. due to twisting movement. When the auto-flex knee brace 10 used as a rotational brake, the auto-flex knee brace 10 will most likely be configured in the pull-pull mode. The amount of rotational resistance can be adjusted by shortening the spring columns (a shorter spring column results in a greater pull and hence greater resistance.).

The human knee is constructed so that ligaments, tendons, and muscles attach the upper articulating femoral section to the lower tibia knee section and serve as a "floating" anchor support system without a fixed, pressed-in-place anchor. Therefore, the angle of the femur bone can be altered by adjusting the spring column assembly's lengths to generate different size forces on each side of the cuffs. The higher thigh angle results in an increased condylar gap on that side of the knee. This allows for customization of the auto-flex knee brace 10 to any bone wear pattern.

FIGS. 32a, 32b, 32c, 32d, 32e and 32f illustrate different views of one embodiment of the auto-flex knee brace 100 that is worn over an extended leg 80 and on a bended knee 82. In this embodiment, one of the spring column assembly may be a solid, non-adjustable spring 102 that can be attached on either the left or right side of the cuffs 12, 14 and other one may be the spring column assembly 20 used in the preferred embodiment. The result is that there will be always a pulling force on the side of the non-adjustable spring 102. Therefore, this supports only the pull-pull or push-pull mode of configuration. When the knee 82 flexes, the non-adjustable extension spring 102 rotates around the screw bindings. The size of the non-adjustable extension spring 102 can be changed to generate different pull forces.

Figure 33A:
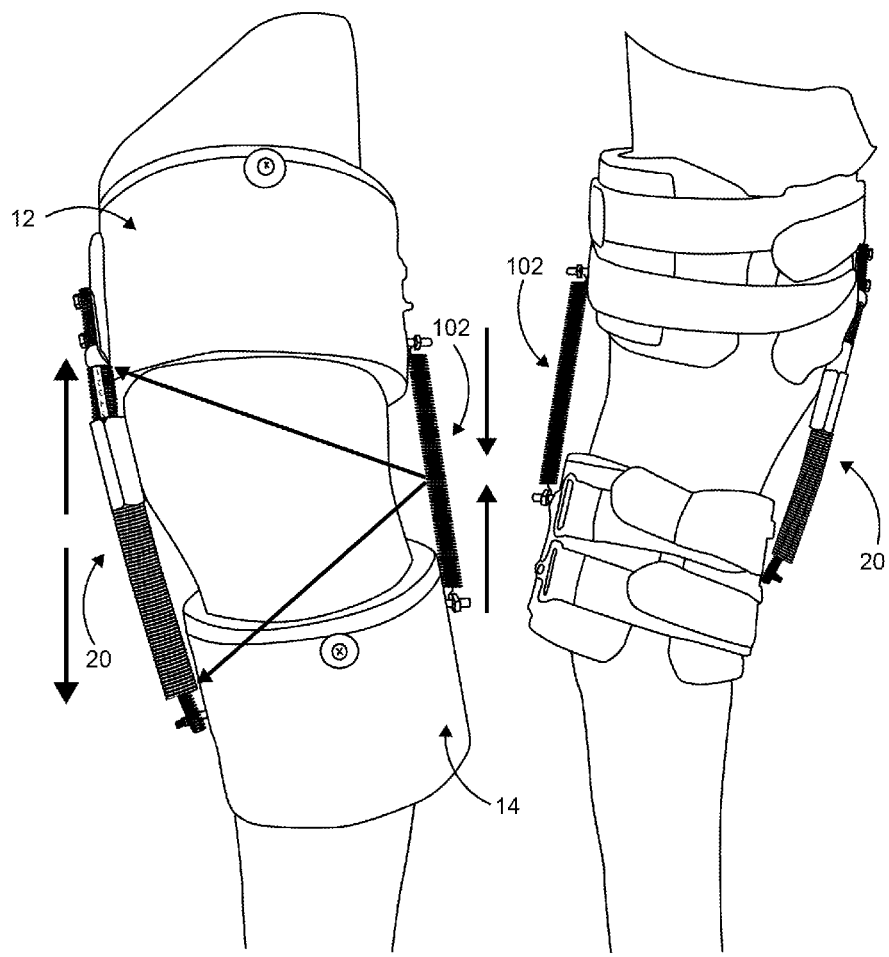
FIG. 33a illustrates a front view and a rear view of the embodiment shown in the FIG. 32a worn over the leg of the user configured in the push-pull mode applied in the offloader clamshell.
Figure 33B:
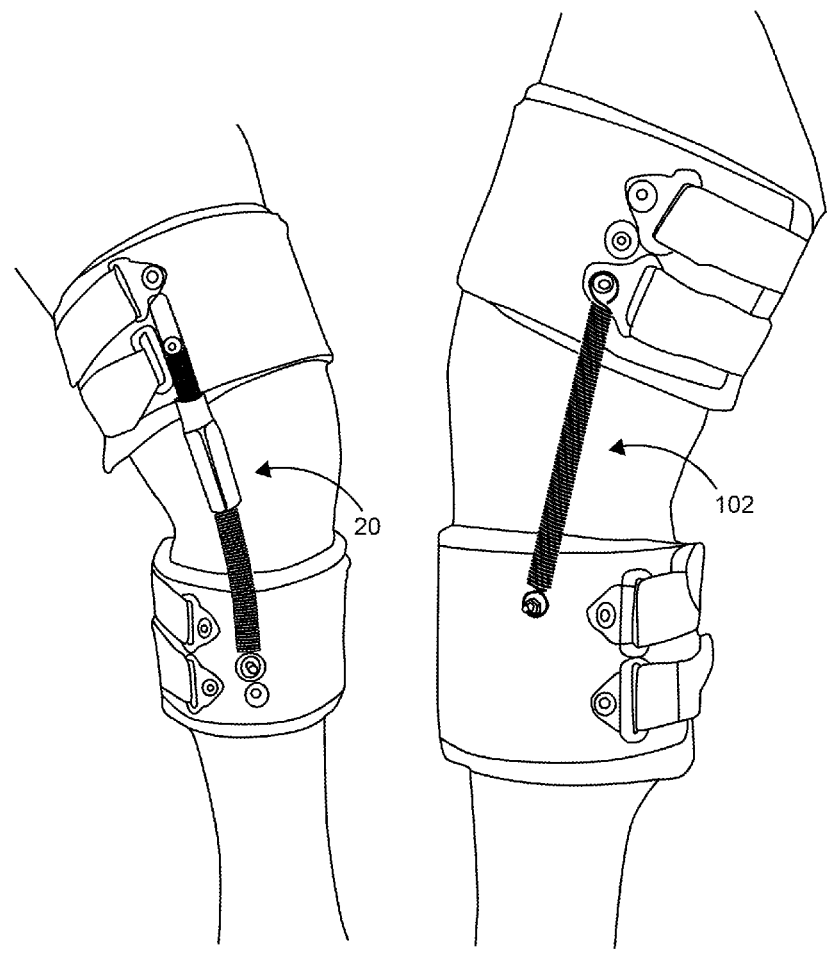
FIG. 33b illustrates a left side view and a right side view of the embodiment shown in the FIG. 32a worn over the leg of the user configured in the push-pull mode applied in the offloader clamshell.
Figure 33C:
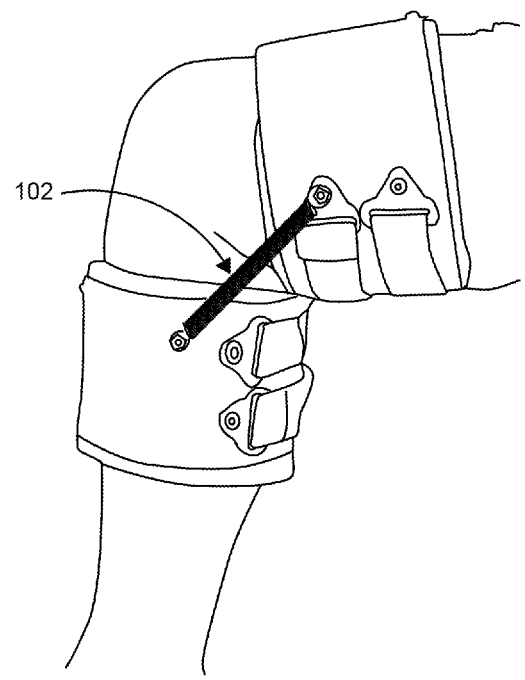
FIG. 33c illustrates a left side view and a right side view of the embodiment shown in the FIG. 32a worn on the bended knee configured in the push-pull mode applied in the offloader clamshell.
Figure 34:
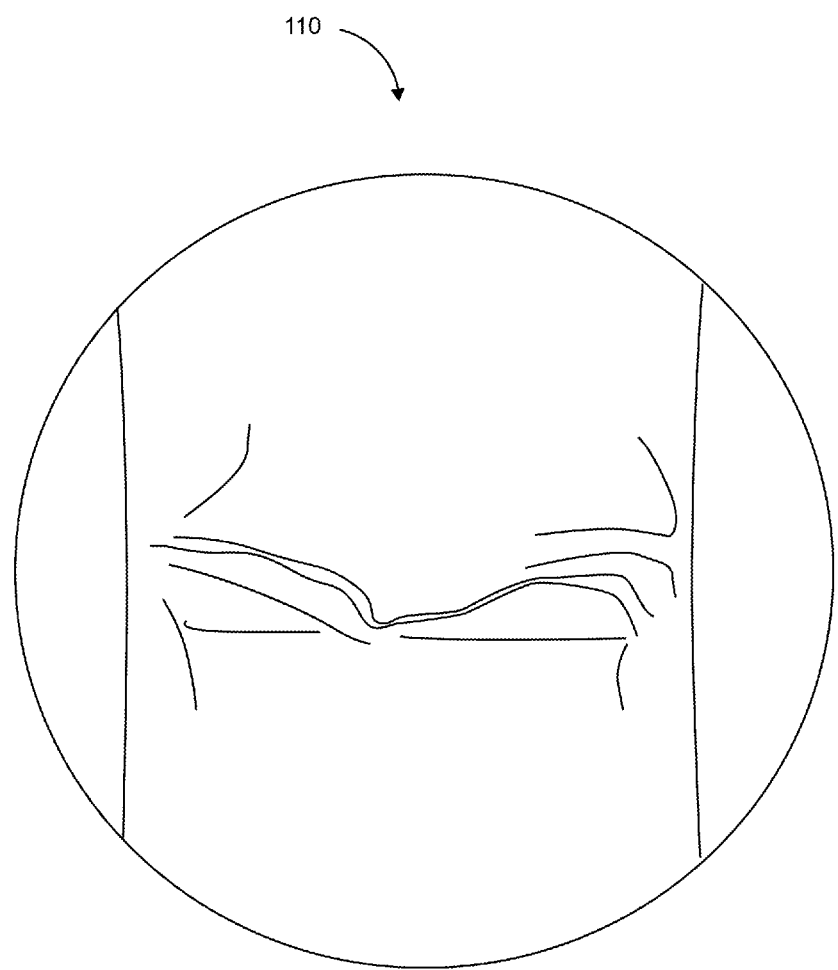
FIG. 34 illustrates the schematic X-ray image shown in FIG. 28 with the use of the embodiment shown in the FIG. 32a configured in the push-pull offloader clamshell mode exerting the maximum force.

FIGS. 33a, 33b and 33c illustrate different views of the embodiment worn over a leg of a user 80 configured in the push-pull mode applied in the offloader clamshell. Here the upper thigh cuffs 12 and the lower thigh cuffs 14 are reversed. FIG. 34 illustrates the schematic X-ray image 110 shown in FIG. 28 with the use of the embodiment shown in the FIG. 32a configured in the push-pull offloader clamshell mode exerting the maximum force.

FIGS. 35a, 35b, 35c and 35d illustrate different views of another embodiment of the auto-flex knee brace 120 that worn on a bended knee 82. In this embodiment, both of the spring column assembly is a solid, non-adjustable spring 122. The result is that there will be always a pulling force on both sides of the non-adjustable spring 122. Therefore, this supports only the pull-pull mode and provides the benefits of the pull-pull mode. For example, in case of the patients with lax ligaments, configuring the brace in pull-pull mode provides measured knee contractual forces to stabilize the knee 82. The non-adjustable spring 122 adjustments are used to determine the optimal amount of tightening force and on each side of the knee 82 and in case of rotational brake, the non-adjustable spring 122 adjustments are used to determine the braking level. This embodiment works both for sports prophylactic braces by inhibiting rotation and for function braces where the objective is to assist lax ligaments. As in the other embodiments with non-adjustable extension springs 122 shown, the extension spring 122 rotates around the screw as the knee 82 flexes. This embodiment works for both prophylactic braces by inhibiting rotation and for function braces where the objective is to assist lax ligaments.

Figure 35A:
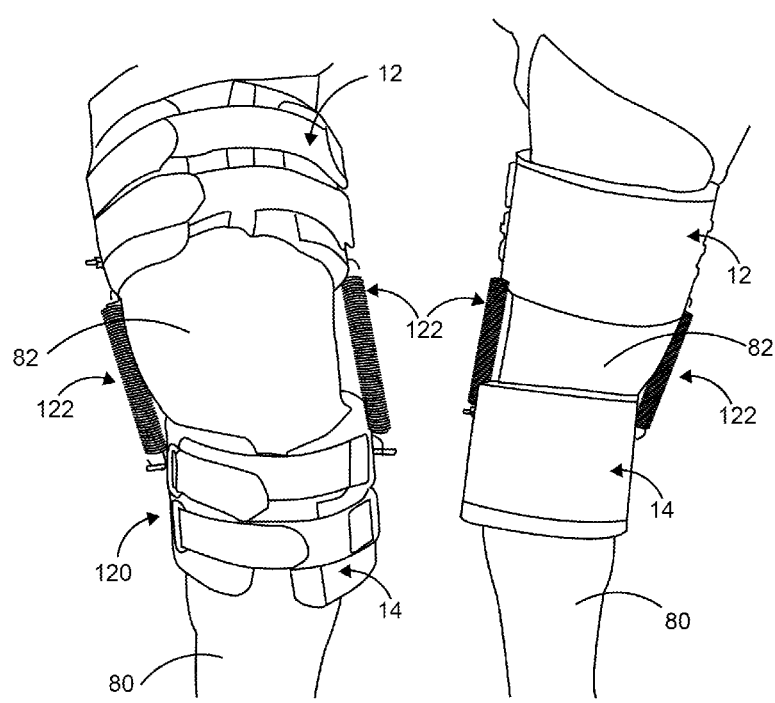
FIG. 35a illustrates a front view and a rear view of another embodiment of the present invention.
Figure 35B:
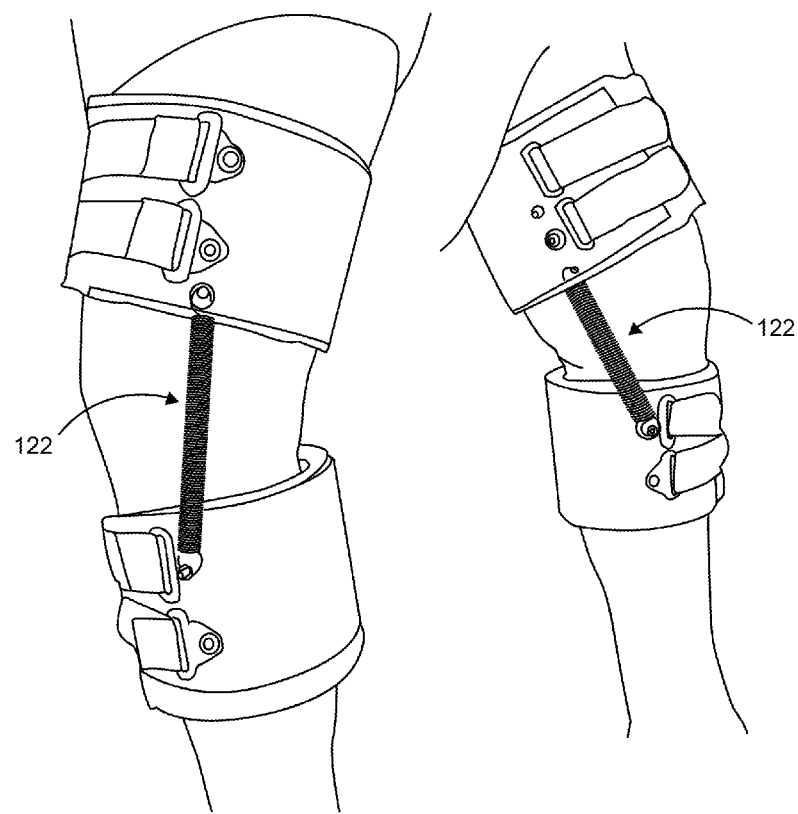
Figure 35C:
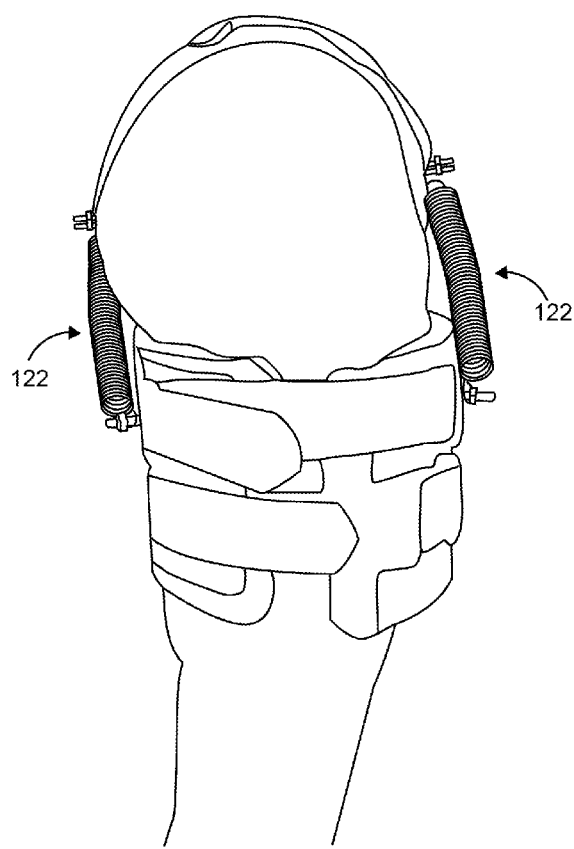
FIG. 35c illustrates a front view of the embodiment shown in the FIG. 35a worn on the bended knee.
Figure 35D:
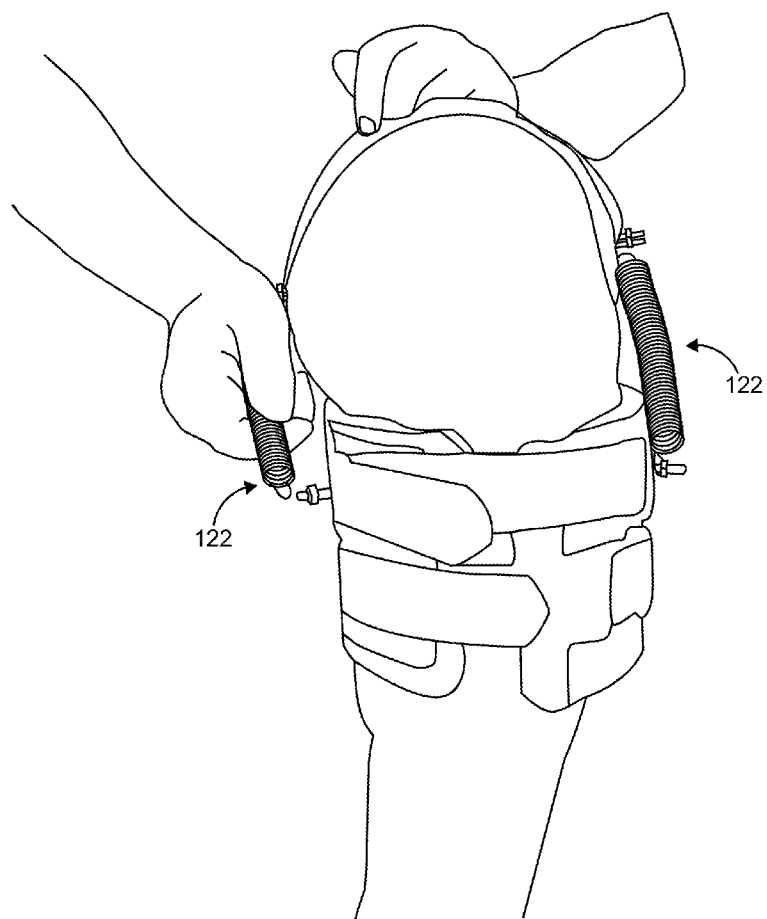
FIG. 35d illustrates a front view of the embodiment shown in the FIG. 35a worn on the bended knee.
Figure 36:
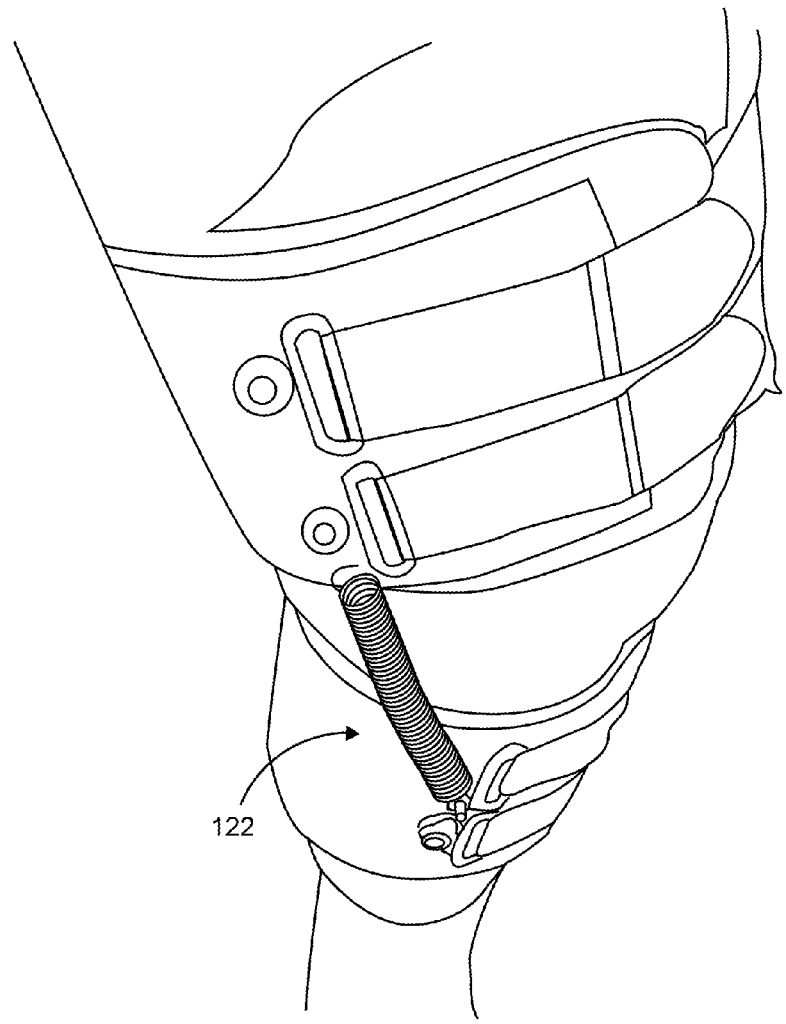
FIG. 36 illustrates a front view of the embodiment shown in the FIG. 35a worn on the bended knee, in which the extension spring is extended from the upper thigh cuff to connect with the lower thigh cuff.
Figure 37A:
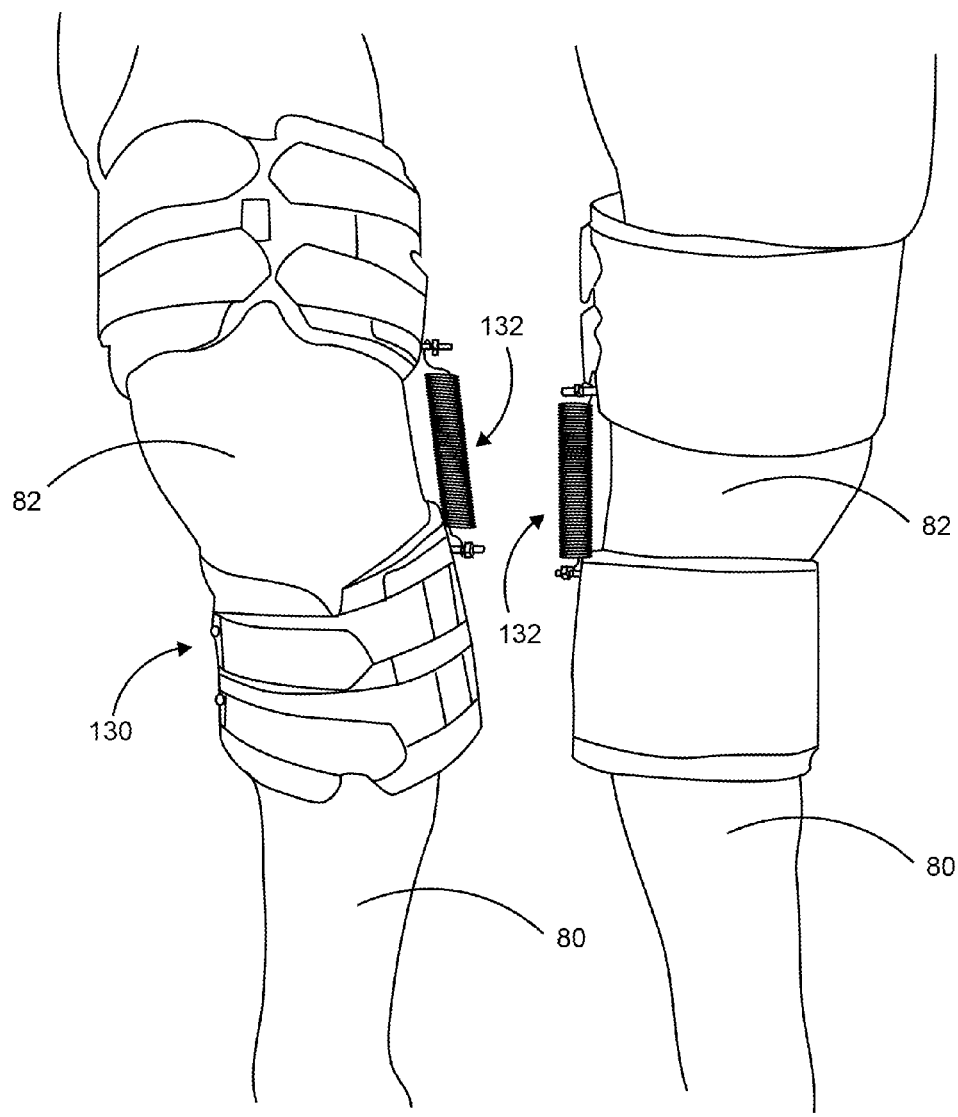
FIG. 37a illustrates a front view and a rear view of yet another embodiment of the present invention.
Figure 37B:
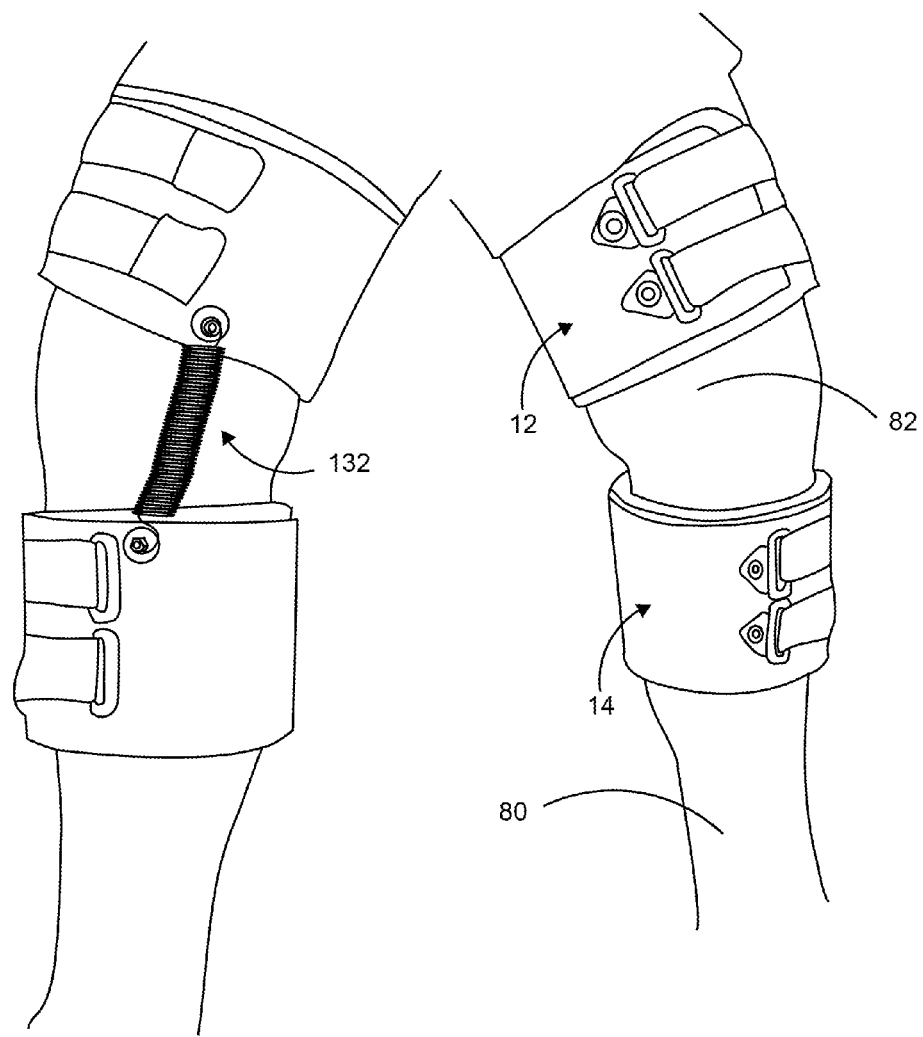
Figure 37C:
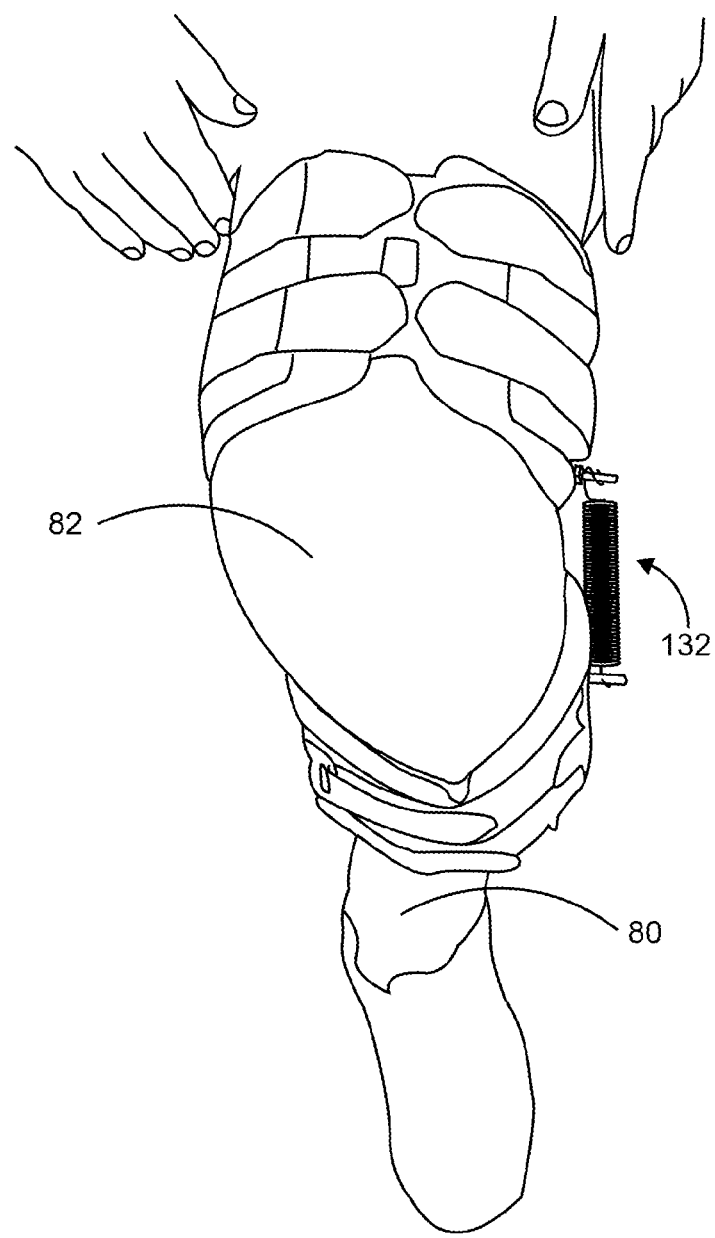
FIG. 37c illustrates a top view of the embodiment shown in the FIG. 37a worn on the bended knee.
Figure 37D:
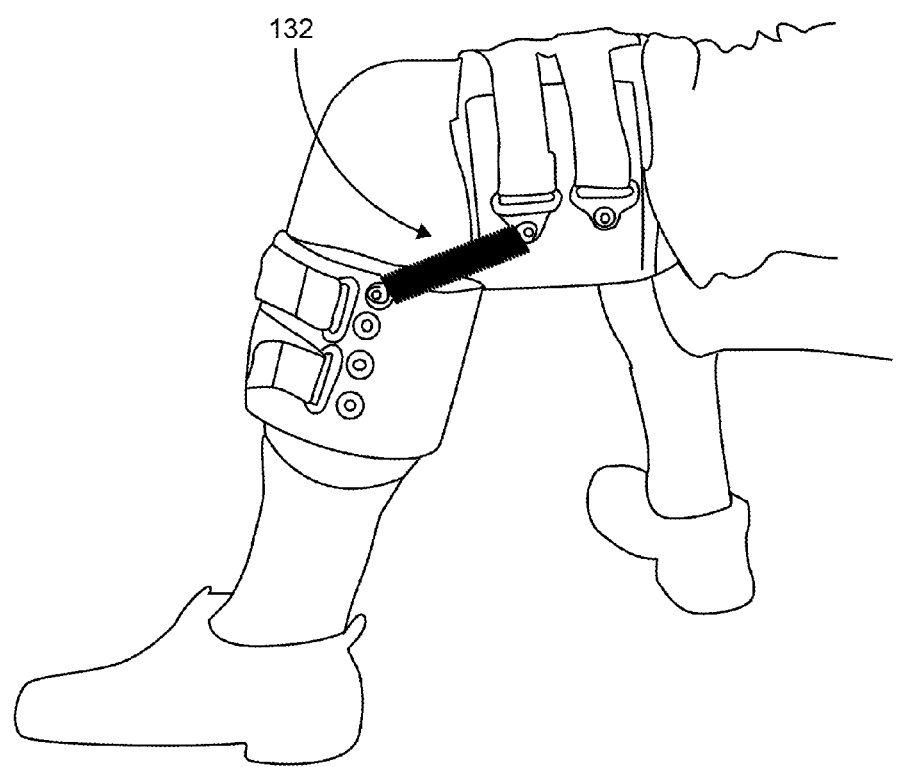
FIG. 37d illustrates a left side view of the embodiment shown in the FIG. 37a worn on the bended knee.

FIG. 36 illustrates a front view of the embodiment shown in the FIG. 35a worn on the bended knee 82, in which the extension spring 122 is extended from the upper thigh cuff 12 to connect with the lower thigh cuff 14.

FIGS. 37a, 37b, 37c, 37d, 37e and 37f illustrate different views of yet another embodiment of the auto-flex knee brace 130 worn on the bended knee 82. In this embodiment, there is only one non-adjustable spring column assembly 132 which is attached either the left side or the right side of the cuffs 12, 14. The result is that there will be always a pulling force on one side of the non-adjustable spring 132 and no force on the other side. This design is still capable of increasing the condylar gap in one of the knee compartments.

While a particular form of the invention has been illustrated and described, it will be apparent that various modifications can be made without departing from the spirit and scope of the invention. For example, the auto-flex knee brace 10 may include other designs for springs and strap arrangements. Accordingly, it is not intended that the invention be limited, except as by the appended claims.

What is claimed is:

1. An auto-flex knee brace comprising:
   an upper thigh cuff positioned substantially above knee for encircling an upper part of leg of a user;
   a lower thigh cuff positioned substantially below the knee for encircling a lower part of the leg of the user;
   a flexible strap arrangement having a first strap means attached to a hinged retainer on the upper thigh cuff and a second strap means attached to a hinged retainer on the lower thigh cuff; and
   at least one spring column assembly releasably coupling the upper thigh cuff and the lower thigh cuff, each of the spring column assembly comprising:
      an extension spring having a proximal end and a distal end;
      a lower cuff connection rod having a pair of terminal ends, one end being threaded and the other end featuring a half flat portion, the cylindrical threaded end being tightly screwed into the proximal end of the extension spring;
      an extension connection rod having a first end, a second end and a longitudinally arranged threaded screw hole, the first end being tightly screwed into the distal end of the extension spring;

an adjustable knob having a threaded compartment and a non threaded compartment separated by a screw hole partition, the non threaded compartment being connected to the second end of the extension connection rod through the threaded screw hole utilizing at least one fastening means; and an upper cuff connection rod having a pair of terminal ends, one end being threaded and the other end featuring a half flat portion, the cylindrical threaded end being tightly screwed into the threaded compartment of the adjustable knob;

whereby the extension spring acts as a flexible hinge and the at least one spring column assembly is configured to mount at different relative vertical positions and modes between the upper thigh cuffs and the lower thigh cuffs thereby achieving a surgery-free way of promoting autogenously as well as supplement-induced knee cartilage cell production in a non-bone-scraping environment.

2. The auto-flex knee brace of claim 1 wherein the at least one fastening means may be a screw.

3. The auto-flex knee brace of claim 1 wherein the half flat portion of the lower cuff connection rod includes at least one screw aperture.

4. The auto-flex knee brace of claim 1 wherein the lower thigh cuff includes a slot having a top notch and a bottom notch.

5. The auto-flex knee brace of claim 1 wherein the lower cuff connection rod slides through the slot and connects to the top notch or the bottom notch through the at least one screw aperture utilizing at least one attachment means.

6. The auto-flex knee brace of claim 1 wherein the cylindrical threaded end of the upper cuff connection rod has a narrow channel region below thread depth lengthwise to accommodate a graduation scale that indicates distance traveled when the adjustable knob is rotated.

7. The auto-flex knee brace of claim 1 wherein the half flat portion of the upper cuff connection rod included a plurality of screw apertures.

8. The auto-flex knee brace of claim 1 wherein the extension spring acts as a multi-axial hinge that changes the bending access automatically to assume a position of least resistance thereby accommodating the entire knee flexion range.

9. The auto-flex knee brace of claim 1 wherein the upper cuff connection rod slides through the slot and connects to the plurality of notches through the plurality of screw apertures utilizing at least one attachment means.

10. The auto-flex knee brace of claim 9 wherein the at least one attachment means may be a screw.

11. The auto-flex knee brace of claim 1 wherein the adjustable knob can be turned for adjusting the length of each of the spring column assembly.

12. The auto-flex knee brace of claim 1 wherein the extension spring acts as a multi-axial hinge that changes their bending axis automatically to assume a position of least resistance thereby accommodates the entire knee flexion range.

13. The auto-flex knee brace of claim 1 wherein the flexible spring column assembly combined with the angled upper cuff connection rod compensates for the misshapen knee curve due to varus/valgus deformities, obesity and thereby provides full support.

14. The auto-flex knee brace of claim 1 wherein the adjustment of the length of each of the spring column assembly determines at least one mode of configuration of the auto-flex knee brace.

15. The auto-flex knee brace of claim 14 wherein the at least one mode of configuration may be a push-push mode in which each of the spring column assembly is attached to the top notch using the at least one attachment means.

16. The auto-flex knee brace of claim 15 wherein during the push-push mode the length of the spring column assembly is reduced using the adjustable knob that pushes both sides of the upper cuffs and both sides of the lower cuffs apart.

17. The auto-flex knee brace of claim 14 wherein the at least one mode of configuration may be a pull-pull mode in which each of the spring column assembly is attached to the bottom notch using the at least one attachment means.

18. The auto-flex knee brace of claim 17 wherein during the pull-pull mode the length of the spring column assembly is reduced using the adjustable knob that pulls both sides of the upper cuffs and both sides of the lower cuffs together.

19. The auto-flex knee brace of claim 1 wherein when the auto-flex knee brace is configured in a pull-pull mode, the knee brace acts as a rotational brake and the springs provide a gradual give nature to limit the slippage of the brace caused by the rotational force thereby preventing twisting injuries.

20. The auto-flex knee brace of claim 14 wherein the at least one mode of configuration may be a push-pull mode in which one of the spring column assembly is attached to the top notch and another spring column assembly is attached to the bottom notch using the at least one attachment means.

21. The auto-flex knee brace of claim 20 wherein during the push-pull mode the length of the spring column assembly attached to the top notch is increased to achieve a push on that side of the cuffs and the length of the spring column assembly attached to the top notch is reduced to achieve pull on that side of the cuffs using the adjustable knob, creating a clamshell effect.

22. The auto-flex knee brace of claim 1 wherein the first strap means and the second strap means is tied around the upper thigh cuff and the lower thigh cuff using a Velcro means.

23. The auto-flex knee brace of claim 1 wherein the upper thigh cuff and the lower thigh cuff includes an extended inner liner material on borders thereof to reduce the pressure generated by the flexible strap arrangement.

24. The auto-flex knee brace of claim 1 wherein the extended inner liner material may be formed from natural gum foam strips.

25. The auto-flex knee brace of claim 1 wherein the extended inner liner material has a high friction silicone rubber contact sheet bonded to the natural gum foam strips providing an additional gripping power to prevent the auto-flex knee brace migration.

26. The auto-flex knee brace of claim 1 wherein the at least one spring column assembly is created from incompressible steel and the at least one spring column assembly in a relaxed state acts as a compressed solid beam thereby providing maximum weight support and flexibility.

27. The auto-flex knee brace of claim 1 wherein the at least one spring column assembly can be replaced by a non-adjustable spring consisting of a simple spring that may be used to implement the pull forces; the size of the non adjustable extension spring is changeable to different pull forces; when the knee flexes, the non adjustable extension spring rotates around the school bindings.

* * * * *